United States Patent
Jackson (12)

(10) Patent No.: US 8,366,745 B2
(45) Date of Patent: Feb. 5, 2013

(54) DYNAMIC STABILIZATION ASSEMBLY HAVING PRE-COMPRESSED SPACERS WITH DIFFERENTIAL DISPLACEMENTS

(76) Inventor: Roger P. Jackson, Prairie Village, KS (US)

(*) Notice: Subject to any disclaimer, the term of this patent is extended or adjusted under 35 U.S.C. 154(b) by 574 days.

(21) Appl. No.: 12/459,492

(22) Filed: Jul. 1, 2009

(65) Prior Publication Data

US 2009/0275985 A1 Nov. 5, 2009

Related U.S. Application Data

(63) Continuation-in-part of application No. 12/148,465, filed on Apr. 18, 2008, and a continuation-in-part of application No. 12/156,260, filed on May 30, 2008, now Pat. No. 7,951,170.

(60) Provisional application No. 61/134,480, filed on Jul. 10, 2008, provisional application No. 61/137,743, filed on Aug. 1, 2008, provisional application No. 60/927,111, filed on May 1, 2007, provisional application No. 60/932,567, filed on May 31, 2007, provisional application No. 60/994,068, filed on Sep. 17, 2007.

(51) Int. Cl.
*A61B 17/70* (2006.01)

(52) U.S. Cl. .................... 606/254; 606/259

(58) Field of Classification Search .......... 606/246–279, 606/86 A; 623/17.11–17.16; 428/188
See application file for complete search history.

(56) References Cited

U.S. PATENT DOCUMENTS

| | | | |
|---|---|---|---|
| 854,956 A | 5/1907 | Martin | |
| 2,243,717 A | 5/1941 | Moreira | |
| 2,346,346 A | 4/1944 | Anderson | |
| 2,362,999 A | 11/1944 | Elmer | |
| 2,531,892 A | 11/1950 | Reese | |
| 2,813,450 A | 11/1957 | Dzus | |
| 3,013,244 A | 12/1961 | Rudy | |
| 3,236,275 A | 2/1966 | Smith | |
| 3,604,487 A | 9/1971 | Gilbert | |
| 3,640,416 A | 2/1972 | Temple | |
| 4,033,139 A | 7/1977 | Frederick | |
| 4,041,939 A | 8/1977 | Hall | |
| 4,190,091 A | 2/1980 | Colognori | |
| 4,373,754 A | 2/1983 | Bollfrass et al. | |
| 4,448,191 A | 5/1984 | Rodnyansky et al. | |
| 4,484,570 A | 11/1984 | Sutter et al. | |
| 4,600,224 A | 7/1986 | Blose | |
| 4,653,486 A | 3/1987 | Coker | |
| 4,703,954 A | 11/1987 | Ortloff et al. | |
| 4,707,001 A | 11/1987 | Johnson | |

(Continued)

FOREIGN PATENT DOCUMENTS

| | | |
|---|---|---|
| CA | 2577436 | 6/2006 |
| DE | G9202745.8 | 4/1992 |

(Continued)

OTHER PUBLICATIONS

*EBI Omega 21* Brochure, EBI Spine Systems, pub. 1999.

(Continued)

*Primary Examiner* — Eduardo C Robert
*Assistant Examiner* — Steven Cotroneo
(74) *Attorney, Agent, or Firm* — John C. McMahon

(57) ABSTRACT

A dynamic longitudinal connecting member assembly includes an anchor member having an integral or otherwise fixed elongate core extending through at least two elastic spacers and at least one outer sleeve or trolley. The anchor member and the outer sleeve each attach to at least one bone anchor. The spacers have differing durometers and/or geometries, resulting in greater axial movement of the sleeve in one direction than in an opposite direction. The spacers are compressed prior to attachment to the bone anchors.

49 Claims, 16 Drawing Sheets

U.S. PATENT DOCUMENTS

| | | |
|---|---|---|
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Barker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | HOlmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,505,731 A | 4/1996 | Tornier |
| 5,507,745 A | 4/1996 | Logroscino et al. |
| 5,496,321 A | 5/1996 | Puno |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,528 A | 3/1998 | Biedermann et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |

| | | |
|---|---|---|
| 6,183,472 B1 | 2/2001 | Lutz |
| 6,186,718 B1 | 2/2001 | Fogard |
| 6,187,005 B1 | 2/2001 | Brace et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Brace et al. |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B1 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Doono et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |

| | | |
|---|---|---|
| 7,044,947 B2 | 2/2006 | Shluzus et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,491,208 B2 | 11/2006 | Pond, Jr. et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |

| | | | |
|---|---|---|---|
| 7,632,292 B2 | 12/2009 | Sengupta et al. | |
| 7,641,673 B2 | 1/2010 | LeCouedic et al. | |
| 7,651,515 B2 | 1/2010 | Mack et al. | |
| 7,655,026 B2 | 2/2010 | Justis et al. | |
| 7,658,739 B2 | 2/2010 | Shluzas | |
| 7,658,752 B2 | 2/2010 | Labrom et al. | |
| 7,682,375 B2 | 3/2010 | Ritland | |
| 7,695,496 B2 | 4/2010 | Labrom et al. | |
| 7,695,498 B2 | 4/2010 | Ritland | |
| 7,695,514 B2 | 4/2010 | Kwak | |
| 7,842,072 B2 * | 11/2010 | Dawson | 606/263 |
| 7,988,710 B2 * | 8/2011 | Jahng et al. | 606/254 |
| 8,029,547 B2 * | 10/2011 | Veldman et al. | 606/257 |
| 6,648,888 B1 | 11/2011 | Shluzas | |
| 6,660,006 B2 | 12/2011 | Markworth et al. | |
| 2001/0001119 A1 | 5/2001 | Lombardo | |
| 2001/0010000 A1 | 7/2001 | Gertzbein | |
| 2001/0023350 A1 | 9/2001 | Choi | |
| 2001/0029375 A1 | 10/2001 | Betz | |
| 2001/0037111 A1 | 11/2001 | Dixon et al. | |
| 2002/0007184 A1 | 1/2002 | Ogilvie et al. | |
| 2002/0013586 A1 | 1/2002 | Justis et al. | |
| 2002/0035366 A1 | 3/2002 | Walder et al. | |
| 2002/0045898 A1 | 4/2002 | Freid et al. | |
| 2002/0058942 A1 | 5/2002 | Biedermann et al. | |
| 2002/0068975 A1 | 6/2002 | Teitelbaum et al. | |
| 2002/0072751 A1 | 6/2002 | Jackson | |
| 2002/0077701 A1 | 6/2002 | Kuslich | |
| 2002/0082602 A1 | 6/2002 | Biedermann et al. | |
| 2002/0095153 A1 | 7/2002 | Jones et al. | |
| 2002/0111626 A1 | 8/2002 | Ralph et al. | |
| 2002/0133159 A1 | 9/2002 | Jackson | |
| 2002/0143341 A1 | 10/2002 | Biedermann et al. | |
| 2002/0173789 A1 | 11/2002 | Howland | |
| 2002/0193795 A1 | 12/2002 | Gertzbein et al. | |
| 2003/0023240 A1 | 1/2003 | Amrein et al. | |
| 2003/0023243 A1 | 1/2003 | Biedermann et al. | |
| 2003/0073996 A1 | 4/2003 | Doubler et al. | |
| 2003/0083657 A1 | 5/2003 | Drewry et al. | |
| 2003/0093078 A1 | 5/2003 | Ritland | |
| 2003/0100896 A1 | 5/2003 | Biedermann et al. | |
| 2003/0105460 A1 | 6/2003 | Crandall et al. | |
| 2003/0109880 A1 | 6/2003 | Shirado et al. | |
| 2003/0114852 A1 | 6/2003 | Biedermann et al. | |
| 2003/0125741 A1 | 7/2003 | Biedermann et al. | |
| 2003/0149432 A1 | 8/2003 | Frigg et al. | |
| 2003/0153911 A1 | 8/2003 | Shluzas | |
| 2003/0163133 A1 | 8/2003 | Altarac et al. | |
| 2003/0171749 A1 | 9/2003 | Le Douedic et al. | |
| 2003/0176862 A1 | 9/2003 | Taylor et al. | |
| 2003/0191470 A1 | 10/2003 | Ritland | |
| 2003/0199873 A1 | 10/2003 | Richelsoph | |
| 2003/0208203 A1 | 11/2003 | Lim et al. | |
| 2003/0208204 A1 | 11/2003 | Bailey et al. | |
| 2003/0212398 A1 | 11/2003 | Jackson | |
| 2003/0216735 A1 | 11/2003 | Altarac et al. | |
| 2003/0220642 A1 | 11/2003 | Freudiger | |
| 2003/0220643 A1 | 11/2003 | Ferree | |
| 2003/0225408 A1 | 12/2003 | Nichols et al. | |
| 2004/0002708 A1 | 1/2004 | Ritland | |
| 2004/0006342 A1 | 1/2004 | Altarac et al. | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0078082 A1 | 4/2004 | Lange | |
| 2004/0220671 A1 | 4/2004 | Ralph et al. | |
| 2004/0087949 A1 | 5/2004 | Bono et al. | |
| 2004/0087952 A1 | 5/2004 | Borgstrom et al. | |
| 2004/0092934 A1 | 5/2004 | Howland | |
| 2004/0097933 A1 | 5/2004 | Lourdel et al. | |
| 2004/0116929 A1 | 6/2004 | Barker et al. | |
| 2004/0133207 A1 | 7/2004 | Abdou | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0147929 A1 | 7/2004 | Biedermann et al. | |
| 2004/0158247 A1 | 8/2004 | Sitiso et al. | |
| 2004/0162560 A1 | 8/2004 | Raynor et al. | |
| 2004/0172022 A1 | 9/2004 | Landry et al. | |

| | | |
|---|---|---|
| 2004/0172025 A1 | 9/2004 | Drewry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0220567 A1 | 11/2004 | Eisermann et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Johng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Splitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 * | 6/2005 | Sicvol et al. ............... 606/61 |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Beidermann et al. |
| 2005/0192571 A1 | 9/2005 | Abdelgany |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brookmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |

| | | |
|---|---|---|
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Falln |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200128 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1* | 11/2006 | White .............................. 606/61 |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Harman |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1* | 5/2007 | Reglos et al. .................... 606/61 |
| 2007/0118117 A1 | 5/2007 | Altarac et al. |
| 2007/0118118 A1 | 5/2007 | Kwak et al. |
| 2007/0118119 A1 | 5/2007 | Nested |

| | | | | | | |
|---|---|---|---|---|---|---|
| 2007/0118122 A1 | 5/2007 | Butler et al. | | 2008/0015586 A1 | 1/2008 | Krishna et al. |
| 2007/0118123 A1 | 5/2007 | Strausbaugh et al. | | 2008/0021454 A1 | 1/2008 | Chao et al. |
| 2007/0118124 A1 | 5/2007 | Biedermann et al. | | 2008/0021455 A1 | 1/2008 | Chao et al. |
| 2007/0123862 A1 | 5/2007 | Warnick | | 2008/0021458 A1 | 1/2008 | Lim |
| 2007/0123864 A1* | 5/2007 | Walder et al. .................. 606/61 | | 2008/0021459 A1 | 1/2008 | Lim |
| 2007/0123865 A1 | 5/2007 | Schlapfer et al. | | 2008/0021462 A1 | 1/2008 | Trieu |
| 2007/0123866 A1 | 5/2007 | Gerbec et al. | | 2008/0021464 A1 | 1/2008 | Norin et al. |
| 2007/0123867 A1 | 5/2007 | Kirschman | | 2008/0021465 A1 | 1/2008 | Shadduck et al. |
| 2007/0123870 A1 | 5/2007 | Jeon et al. | | 2008/0021466 A1 | 1/2008 | Shadduck et al. |
| 2007/0123871 A1 | 5/2007 | Jahng | | 2008/0021473 A1 | 1/2008 | Butler et al. |
| 2007/0129729 A1* | 6/2007 | Petit et al. ................... 606/61 | | 2008/0027432 A1 | 1/2008 | Strauss et al. |
| 2007/0135815 A1 | 6/2007 | Gerbec et al. | | 2008/0033435 A1 | 2/2008 | Studer et al. |
| 2007/0161986 A1 | 7/2007 | Levy | | 2008/0039838 A1 | 2/2008 | Landry et al. |
| 2007/0161991 A1 | 7/2007 | Altarac et al. | | 2008/0039843 A1 | 2/2008 | Abdou |
| 2007/0161994 A1 | 7/2007 | Lowrey et al. | | 2008/0045951 A1 | 2/2008 | Fanger et al. |
| 2007/0161995 A1 | 7/2007 | Trautwein et al. | | 2008/0045955 A1 | 2/2008 | Berrevoets et al. |
| 2007/0161996 A1 | 7/2007 | Biedermann et al. | | 2008/0045957 A1 | 2/2008 | Landry et al. |
| 2007/0161997 A1 | 7/2007 | Thramann et al. | | 2008/0051780 A1 | 2/2008 | Vaidya et al. |
| 2007/0161999 A1 | 7/2007 | Biedermann et al. | | 2008/0051787 A1 | 2/2008 | Remington et al. |
| 2007/0167948 A1 | 7/2007 | Abdou | | 2008/0058811 A1 | 3/2008 | Alleyne et al. |
| 2007/0167949 A1 | 7/2007 | Altarac et al. | | 2008/0058812 A1 | 3/2008 | Zehnder |
| 2007/0173818 A1 | 7/2007 | Hested et al. | | 2008/0065071 A1 | 3/2008 | Park |
| 2007/0173819 A1 | 7/2007 | Sandlin | | 2008/0065073 A1 | 3/2008 | Perriello et al. |
| 2007/0173820 A1 | 7/2007 | Trieu | | 2008/0065075 A1 | 3/2008 | Dant |
| 2007/0173822 A1 | 7/2007 | Bruneau et al. | | 2008/0065077 A1 | 3/2008 | Ferree |
| 2007/0173828 A1 | 7/2007 | Firkins et al. | | 2008/0065079 A1 | 3/2008 | Bruneau et al. |
| 2007/0173832 A1 | 7/2007 | Tebbe et al. | | 2008/0071273 A1 | 3/2008 | Hawkes et al. |
| 2007/0191839 A1 | 8/2007 | Justis et al. | | 2008/0071274 A1 | 3/2008 | Ensign |
| 2007/0191841 A1 | 8/2007 | Justis et al. | | 2008/0071277 A1 | 3/2008 | Warnick |
| 2007/0191846 A1 | 8/2007 | Bruneau et al. | | 2008/0077139 A1 | 3/2008 | Landry et al. |
| 2007/0198014 A1 | 8/2007 | Graf et al. | | 2008/0086131 A1 | 4/2008 | Daly et al. |
| 2007/0123720 A1 | 9/2007 | Gordon et al. | | 2008/0086132 A1 | 4/2008 | Biedermann et al. |
| 2007/0208344 A1 | 9/2007 | Young | | 2008/0091214 A1 | 4/2008 | Richelsoph |
| 2007/0213720 A1 | 9/2007 | Gordon et al. | | 2008/0097431 A1 | 4/2008 | Vessa |
| 2007/0225707 A1 | 9/2007 | Wisnewski et al. | | 2008/0097434 A1 | 4/2008 | Moumene et al. |
| 2007/0225708 A1 | 9/2007 | Biedermann et al. | | 2008/0097441 A1 | 4/2008 | Hayes et al. |
| 2007/0225710 A1 | 9/2007 | Jahng et al. | | 2008/0097457 A1 | 4/2008 | Warnick |
| 2007/0225711 A1 | 9/2007 | Ensign | | 2008/0108992 A1 | 5/2008 | Barry et al. |
| 2007/0233064 A1 | 10/2007 | Holt | | 2008/0119858 A1 | 5/2008 | Potash |
| 2007/0233073 A1 | 10/2007 | Wisnewski et al. | | 2008/0125777 A1 | 5/2008 | Veldman et al. |
| 2007/0233075 A1 | 10/2007 | Dawson | | 2008/0125787 A1 | 5/2008 | Doubler et al. |
| 2007/0233078 A1 | 10/2007 | Justis et al. | | 2008/0132952 A1 | 6/2008 | Malandain et al. |
| 2007/0233080 A1 | 10/2007 | Na et al. | | 2008/0140075 A1 | 6/2008 | Ensign et al. |
| 2007/0233085 A1 | 10/2007 | Biedermann et al. | | 2008/0140076 A1 | 6/2008 | Jackson |
| 2007/0233086 A1 | 10/2007 | Harms et al. | | 2008/0140133 A1 | 6/2008 | Allard et al. |
| 2007/0233087 A1 | 10/2007 | Schlapfer | | 2008/0147122 A1 | 6/2008 | Jackson |
| 2007/0233092 A1 | 10/2007 | Falahee | | 2008/0154307 A1 | 6/2008 | Colleran et al. |
| 2007/0233094 A1 | 10/2007 | Colleran et al. | | 2008/0234744 A1 | 6/2008 | Zylber et al. |
| 2007/0233095 A1 | 10/2007 | Schlaepfer | | 2008/0161854 A1 | 7/2008 | Bae et al. |
| 2007/0250061 A1 | 10/2007 | Chin et al. | | 2008/0161859 A1 | 7/2008 | Nilsson |
| 2007/0124249 A1 | 11/2007 | Lim et al. | | 2008/0161863 A1 | 7/2008 | Arnold et al. |
| 2007/0260243 A1 | 11/2007 | Kagami | | 2008/0167687 A1 | 7/2008 | Colleran et al. |
| 2007/0270806 A1 | 11/2007 | Foley et al. | | 2008/0177316 A1 | 7/2008 | Bergeronk et al. |
| 2007/0270807 A1 | 11/2007 | Armstrong et al. | | 2008/0177317 A1 | 7/2008 | Jackson |
| 2007/0270810 A1 | 11/2007 | Sanders | | 2008/0177319 A1 | 7/2008 | Schwab |
| 2007/0270813 A1 | 11/2007 | Garamszegi | | 2008/0177321 A1 | 7/2008 | Drewry et al. |
| 2007/0270814 A1 | 11/2007 | Lim et al. | | 2008/0177322 A1 | 7/2008 | Davis et al. |
| 2007/0270815 A1 | 11/2007 | Johnson et al. | | 2008/0177327 A1 | 7/2008 | Malandain et al. |
| 2007/0270821 A1 | 11/2007 | Trieu et al. | | 2008/0183212 A1 | 7/2008 | Veldman et al. |
| 2007/0270830 A1 | 11/2007 | Morrison | | 2008/0183213 A1 | 7/2008 | Veldman et al. |
| 2007/0270831 A1 | 11/2007 | Dewey et al. | | 2008/0183215 A1 | 7/2008 | Altarac et al. |
| 2007/0270832 A1 | 11/2007 | Moore | | 2008/0183216 A1 | 7/2008 | Jackson |
| 2007/0270835 A1 | 11/2007 | Wisnewski | | 2008/0183219 A1 | 7/2008 | Bertram |
| 2007/0270837 A1 | 11/2007 | Eckhardt et al. | | 2008/0183223 A1 | 7/2008 | Jeon et al. |
| 2007/0270838 A1 | 11/2007 | Bruneau et al. | | 2008/0195100 A1 | 8/2008 | Capote et al. |
| 2007/0270839 A1 | 11/2007 | Jeon et al. | | 2008/0195153 A1 | 8/2008 | Thompson |
| 2007/0270843 A1 | 11/2007 | Matthis et al. | | 2008/0215095 A1 | 9/2008 | Biedermann et al. |
| 2007/0276380 A1* | 11/2007 | Jahng et al. ................. 606/61 | | 2008/0221620 A1 | 9/2008 | Krause |
| 2007/0288004 A1 | 12/2007 | Alvarez | | 2008/0221692 A1 | 9/2008 | Zucherman et al. |
| 2007/0288008 A1 | 12/2007 | Park | | 2008/0228227 A1 | 9/2008 | Brown et al. |
| 2007/0288009 A1 | 12/2007 | Logan | | 2008/0228229 A1 | 9/2008 | Walder et al. |
| 2007/0288011 A1* | 12/2007 | Logan ........................... 606/61 | | 2008/0234691 A1* | 9/2008 | Schwab .................... 606/100 |
| 2007/0288012 A1 | 12/2007 | Colleran et al. | | 2008/0234734 A1 | 9/2008 | Wabler et al. |
| 2008/0009862 A1 | 1/2008 | Hoffman | | 2008/0234736 A1 | 9/2008 | Trieu et al. |
| 2008/0009864 A1 | 1/2008 | Forton et al. | | 2008/0234737 A1* | 9/2008 | Boschert .................... 606/254 |
| 2008/0015578 A1 | 1/2008 | Erickson et al. | | 2008/0234739 A1 | 9/2008 | Hudgins et al. |
| 2008/0015579 A1 | 1/2008 | Whipple | | 2008/0234746 A1 | 9/2008 | Jahng et al. |
| 2008/0015580 A1 | 1/2008 | Chao | | 2008/0243188 A1 | 10/2008 | Walder |
| 2008/0015584 A1 | 1/2008 | Richelsoph | | 2008/0255617 A1 | 10/2008 | Cho et al. |

| | | |
|---|---|---|
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2009/0005817 A1* | 1/2009 | Friedrich et al. ............... 606/246 |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hested et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durwood et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240285 A1* | 9/2009 | Friedrich et al. ............... 606/255 |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0094348 A1 | 4/2010 | Biedermann et al. |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |

| | | |
|---|---|---|
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica SpineTech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
*Spine*, Lipcott, Williams & Wilkins, Inc. vol. 24, No. 15, p. 1495.
Brochure of Tyco/Healthcare/Surgical Dynamics on Spiral Radius 90D, Publication Date: Sep. 2001, pp. 1-8.
Brochure of Sofamor Danek the Spine Specialist, TSRH, Pedicle Screw Spinal System, Publication Date: Jan. 23, 1995.
Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
Brochure of Zimmer Spine, Inc., Dynesys® LIS Less Invasive Surgery, The Dynamic Stabilization System, Publication Date: 2005.

\* cited by examiner

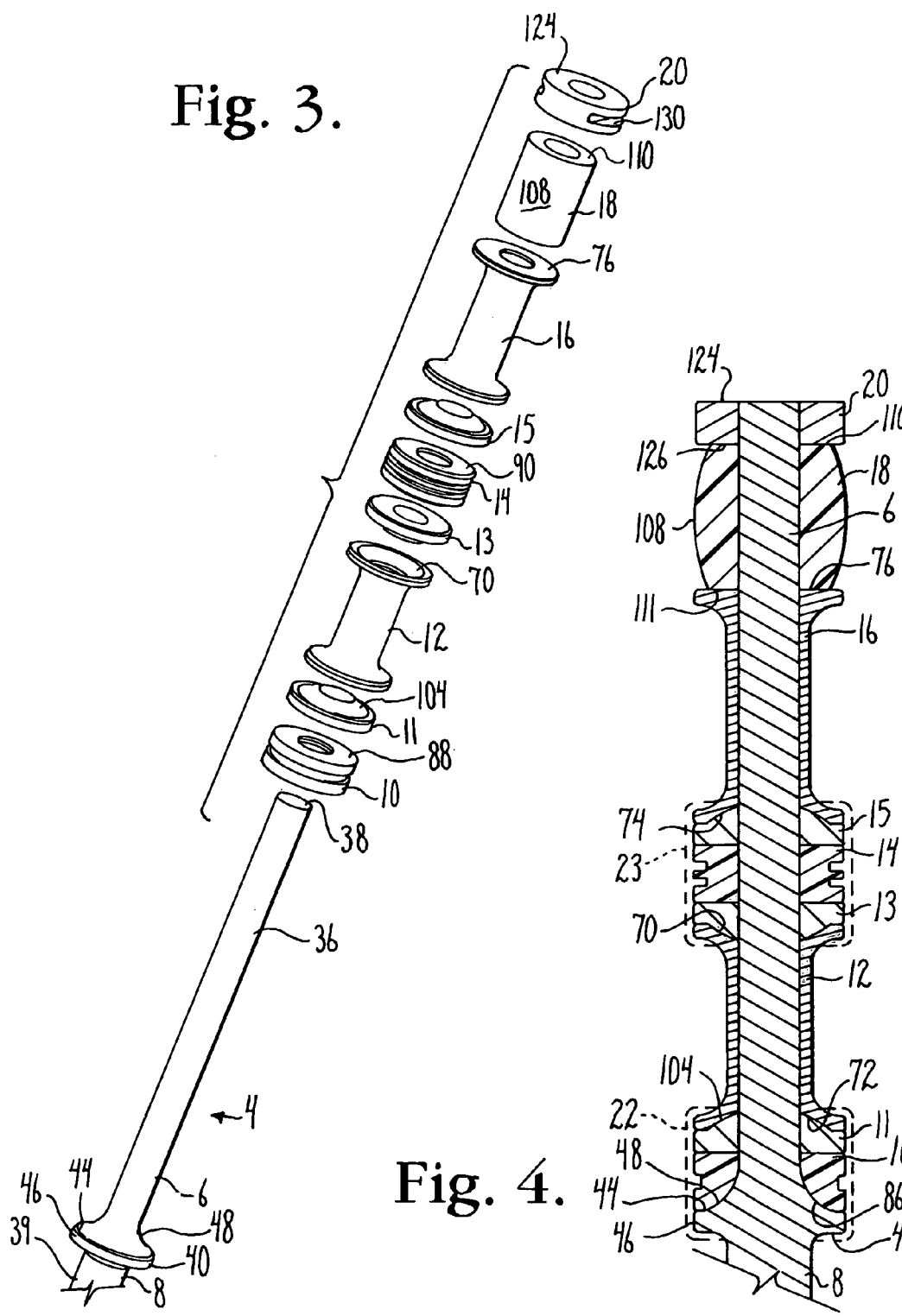

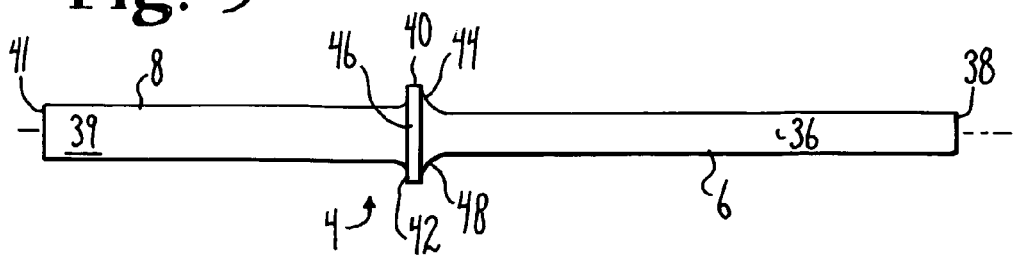
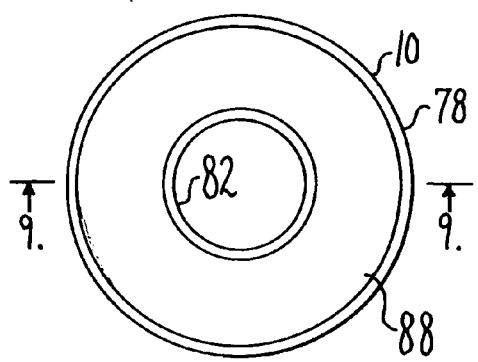
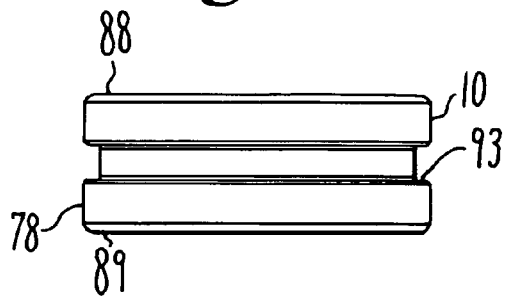
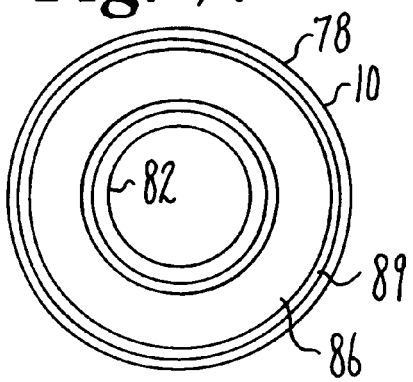
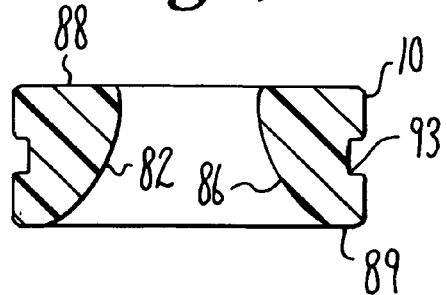

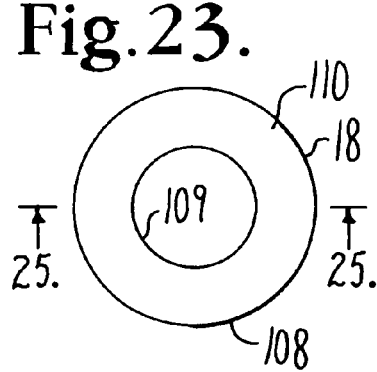
Fig.23.
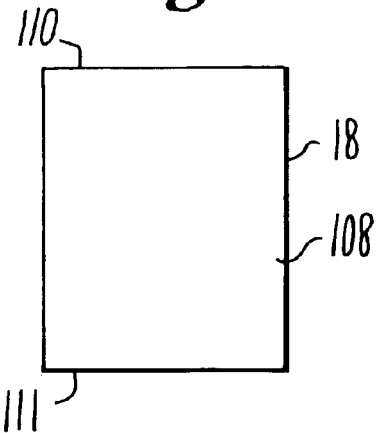
Fig.24.
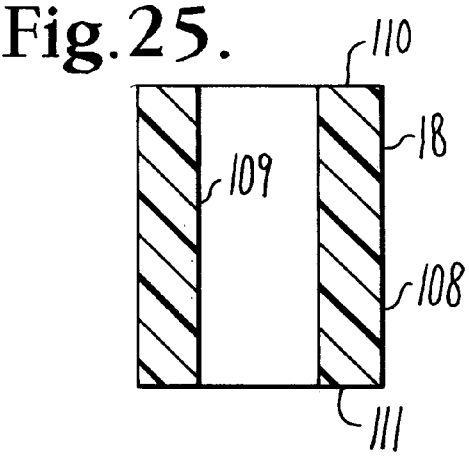
Fig.25.
Fig.27.
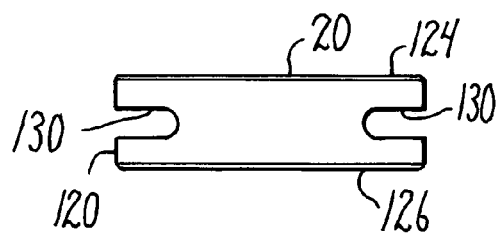
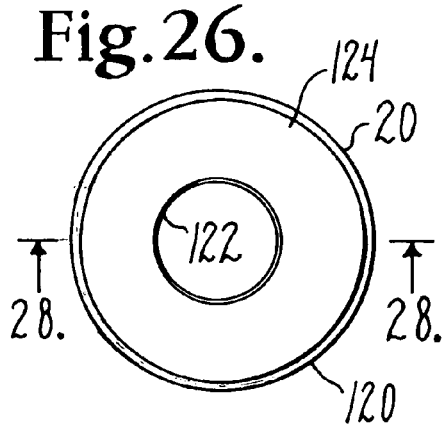
Fig.26.
Fig.28.
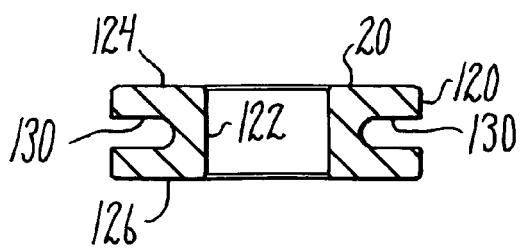

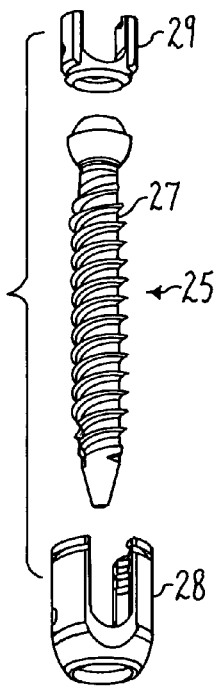
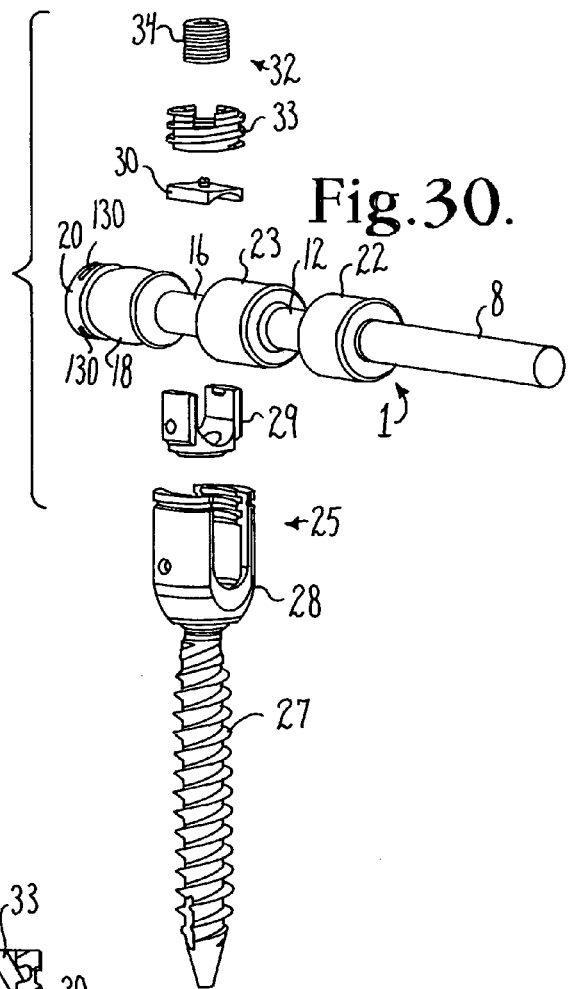
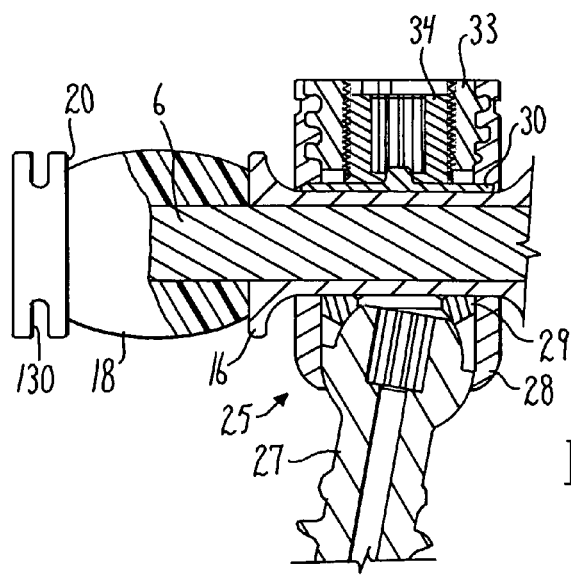
Fig.29.
Fig.30.
Fig.31.

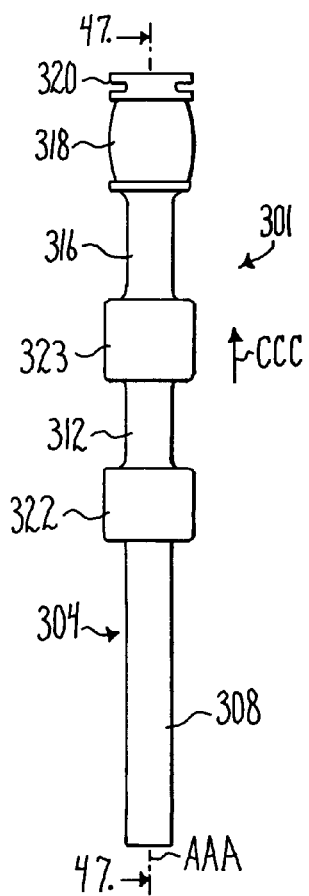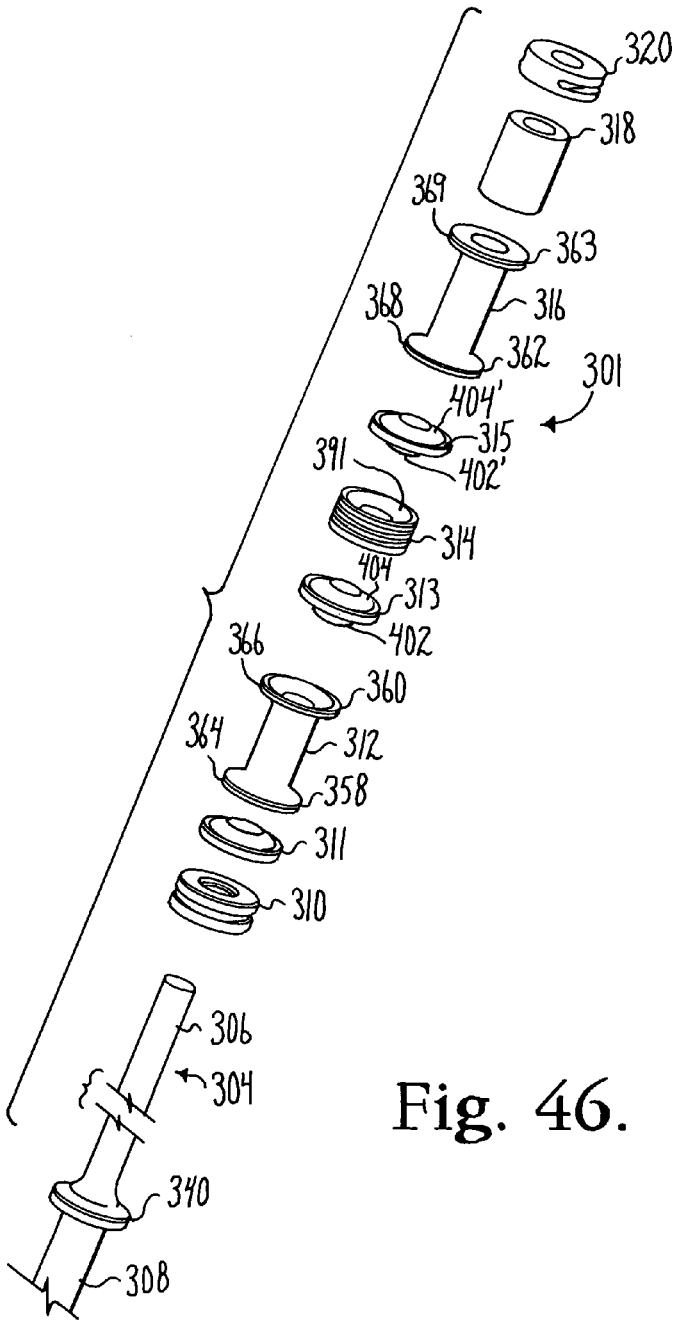
Fig. 45.
Fig. 46.

DYNAMIC STABILIZATION ASSEMBLY HAVING PRE-COMPRESSED SPACERS WITH DIFFERENTIAL DISPLACEMENTS

CROSS-REFERENCE TO RELATED APPLICATIONS

This application claims the benefit of U.S. Provisional Patent Application Ser. No. 61/134,480, filed Jul. 10, 2008 and claims the benefit of U.S. Provisional Patent Application Ser. No. 61/137,743, filed Aug. 1, 2008, both of which are incorporated by reference herein. This application is also a continuation-in-part of U.S. patent application Ser. No. 12/148,465, filed Apr. 18, 2008, that claims the benefit of U.S. Provisional Patent Application Ser. No. 60/927,111, filed May 1, 2007, both of which are incorporated by reference herein. This application is also a continuation-in-part of U.S. patent application Ser. No. 12/156,260, filed May 30, 2008, that claims the benefit of U.S. Provisional Patent Application Ser. No. 60/932,567, filed May 31, 2007, and the benefit of U.S. Provisional Patent Application Ser. No. 60/994,068, filed Sep. 17, 2007, all three of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (flexion, extension and lateral), torsion, shear, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially inelastic rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, side bending, distraction, compression and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Shear forces are not well resisted by the typical cord and spacer stabilization systems. Such tensioned cord and spacer systems may also cause facet joint compression during spinal movement, especially flexion.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

A longitudinal connecting member assembly according to the invention has an inner elongate core of circular or non-circular cross-section that is integral or otherwise fixed to a first bone anchor attachment portion. A first elastic spacer surrounds the core and is slidable along the core at a location between a pair of adjacent bone anchors. At least one outer inelastic sleeve or tube-like trolley member also surrounds the core and is in sliding relationship with the core. The outer sleeve also engages at least one bone anchor. A second elastic spacer of durometer or geometry differing from the first elastic spacer also surrounds the core and is located at a side of the at least one sleeve member opposite the first elastic spacer. The inner core, elastic spacers and inelastic sleeve or sleeves cooperate dynamically, with the spacers being at least somewhat pre-compressed resulting in little-to-no or more substantial deformation of the spacers prior to insertion, and controlling movement of the sleeve allowing greater travel of the sleeve along the core in a single direction; for example, advantageously allowing greater operative travel of the sleeve in a cephalad or cranial direction and more limited movement in a caudal or caudad direction after insertion. In addition, in certain embodiments, the sleeve or tube trolley members feature inner surfaces having non-linear relief for improved core member function with respect to bending stress, wear and fatigue life concerns.

OBJECTS AND ADVANTAGES OF THE INVENTION

An object of the invention is to provide dynamic medical implant stabilization assemblies having longitudinal connecting members that include a flexible, pre-tensioned portion that can allow for controlled bending, torsion, compression and distraction of the assembly. Another object of the invention is to provide such an assembly including elastic pre-compressed spacers of various durometers and/or geometries. A further object of the invention is to provide dynamic medical implant longitudinal connecting members that may be utilized with a variety of bone screws, hooks and other bone anchors. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is an enlarged and partial exploded perspective view of the assembly of FIG. 1 including a solid core anchor, a first differential compression spacer, a first pressure washer, a first sleeve, a second pressure washer, a second differential compression spacer, a third pressure washer, a second sleeve, an elastic bumper and a crimping ring.

FIG. 4 is an enlarged and partial cross-sectional view taken along the line 4-4 of FIG. 1 and with two optional over-molded coverings shown in phantom.

FIG. 5 is an enlarged side elevational view of the solid core anchor of FIG. 3.

FIG. 6 is an enlarged top plan view of the first differential compression spacer of FIG. 3.

FIG. 7 is an enlarged bottom plan view of the first spacer of FIG. 3.

FIG. 8 is an enlarged side elevational view of the first spacer of FIG. 3.

FIG. 9 is an enlarged cross-sectional view taken along the line 9-9 of FIG. 6.

FIG. 23 is an enlarged top plan view of the bumper of FIG. 3.

FIG. 24 is an enlarged side elevational view of the bumper of FIG. 3.

FIG. 25 is an enlarged cross-sectional view taken along the line 25-25 of FIG. 23.

FIG. 26 is an enlarged top plan view of the crimping ring of FIG. 3.

FIG. 27 is an enlarged side elevational view of the crimping ring of FIG. 3.

FIG. 28 is an enlarged cross-sectional view taken along the line 28-28 of FIG. 26.

FIG. 29 is an enlarged exploded perspective view of a portion of one of the bone screws shown in FIG. 2.

FIG. 30 is an enlarged perspective view of the connecting member of FIG. 1 shown with one of the bone screws of FIG. 2 in exploded perspective view.

FIG. 31 is an enlarged and partial side elevational view of the assembly of FIG. 1, shown with a bone screw of FIG. 2, with portions broken away to show the detail thereof.

FIG. 45 is an enlarged side elevational view of a third embodiment of a dynamic connecting member assembly according to the invention.

FIG. 46 is a reduced and partial exploded perspective view of the assembly of FIG. 45.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

Figure 1:
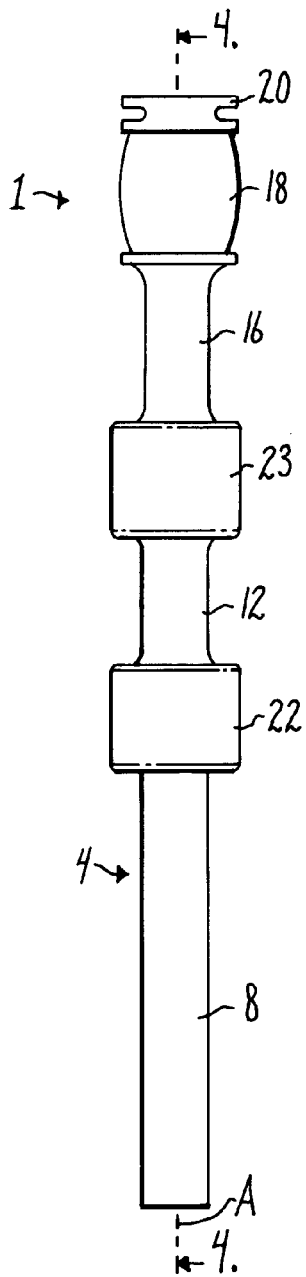
FIG. 1 is an enlarged side elevational view of a dynamic fixation connecting member assembly according to the invention.
Figure 2:
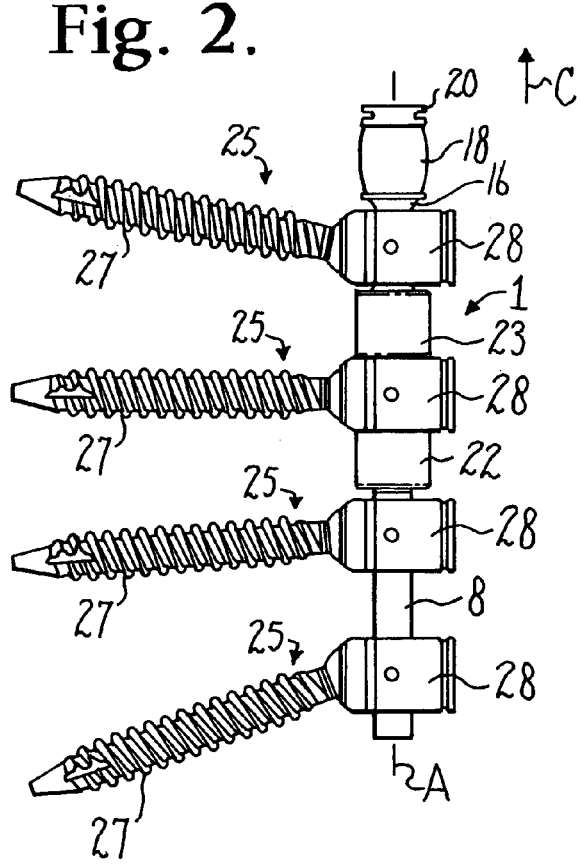
FIG. 2 is a reduced side elevational view of the assembly of FIG. 1 shown with four bone screws and in an operative position with respect to a human spine.

With reference to FIGS. 1-37, the reference numeral 1 generally designates a non-fusion dynamic stabilization longitudinal connecting member assembly according to the present invention. The connecting member assembly 1 includes an inelastic anchor member, generally 4, having an inelastic elongate inner core 6 extending from a bone anchor attachment portion 8; a first elastic differential compression spacer 10; a first hard or inelastic contoured pressure washer 11; a first inelastic sleeve or sleeve trolley 12; a second inelastic contoured pressure washer 13; a second elastic differential compression spacer 14; a third inelastic contoured pressure washer 15; a second inelastic sleeve 16; a third elastic differential compression spacer or elastic bumper 18; and an inelastic crimping ring 20; all substantially symmetrically aligned with respect to a central axis A of the anchor member 4. The elongate core 6 of the anchor member 4 is receivable within the spacers, sleeves, pressure washers, bumper and crimping ring. Thus, the axis A of the anchor member 4 is also the axis of the fully assembled assembly 1. An optional over-molded sleeve or casing 22 can surround a portion of the anchor member 4 extending to the bone anchor attaching portion 8, the spacer 10, the washer 11 and a portion of the sleeve 12. A second over-molded sleeve or casing 23 surrounds a portion of the sleeve 12, the washer 13, the spacer 14, the washer 15 and a portion of the sleeve 16. As will be described in greater detail below, when fully assembled and all components fixed in position, as shown in FIGS. 1, 2 and 4, for example, the spacers 10 and 14 and the bumper 18 are in compression, with the more elastic bumper 18 shown being slightly deformed and bulging outwardly due to the compressive force placed thereupon. The pre-compressed spacers and bumpers in turn place axial forces upon the sleeves 12 and 16, the sleeves thus being in a dynamic relationship with the spacers and movable with respect to the core. In particular, FIG. 2 illustrates placement of the assembly 1 and cooperating bone screws as positioned along a human spine with the elastic bumper 18 being at a top or upper position, the bumper 18 and spacers 10 and 14 having varying elasticities to allow for more movement of the assembly 1 in a cephalad or cranial direction and more limited movement in a caudad direction.

As illustrated in FIG. 2, the dynamic connecting member assembly 1 cooperates with at least three bone anchors and is illustrated with four bone anchors in the form of polyaxial bone screws, generally 25, the assembly 1 being captured and fixed in place at the anchor portion 8, the inelastic sleeve 12 and the inelastic sleeve 16 by the bone screws 25. Because the anchor portion 8 and the sleeves 12 and 16 have substantially solid, substantially hard, inelastic cylindrical surfaces, the connecting member assembly 1 may be used with a wide variety of bone screws and other bone anchors already available for cooperation with more rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, external or internal drives, break-off tops and inner set screws. The bone anchors, closure structures and the connecting member assembly 1 are then operably incorporated in an overall spinal implant system for correcting degenerative conditions, deformities, injuries, or defects to the spinal column of a patient.

In the particular embodiment of the assembly 1 being illustrated herein, wherein the sleeves 12 and 16 are advantageously relatively thin so as to result in an assembly having a low profile, the bone screws 25 are equipped with upper and lower pressure inserts to closely hold the sleeves and yet not crush the sleeves against the inner core 6. In particular, with reference to FIGS. 29, 30 and 31, the illustrated polyaxial screws 25 each include a shank 27, a receiver or head 28, a lower pressure insert 29, an upper pressure insert 30 and a closure structure, generally 32 that further includes and outer fastener 33 and an inner set screw 34. The illustrated shank 27 for insertion into a vertebra (not shown) is pivotally attached to the open receiver or head 28. The shank 27 includes a threaded outer surface and optionally includes a central cannula or through-bore disposed along an axis of rotation of the shank 27. The through bore provides a passage through the shank interior for a length of wire or pin inserted into the vertebra prior to the insertion of the shank 27, the wire or pin providing a guide for insertion of the shank 27 into the vertebra. The receiver 28 includes a pair of spaced and generally parallel arms that form an open generally U-shaped channel therebetween that is open at distal ends of such arms. The receiver arms each include radially inward or interior surfaces that have a discontinuous guide and advancement structure mateable with cooperating structure on the outer fastener 33. The guide and advancement structure may be a partial helically wound flangeform configured to mate under rotation with a similar structure on the outer fastener 33 or a buttress thread, a square thread, a reverse angle thread or other thread like or non-thread like helically wound advancement structures for operably guiding under rotation and advancing the fastener 33 downward between the receiver arms and having such a nature as to resist splaying of the receiver arms when the fastener 33 is advanced between the receiver arms.

The illustrated shank 27 is top loaded into the receiver 28 and has a curved head for sliding, pivotal engagement with an inner surface of the receiver 28. However, a variety of polyaxial connections may be possible. For example, a spline capture connection as described in U.S. Pat. No. 6,716,214, and incorporated by reference herein, may be used wherein the bone screw shank includes a capture structure mateable with a retaining structure disposed within the receiver. The retaining structure includes a partially spherical surface that is slidingly mateable with a cooperating inner surface of the receiver, allowing for a wide range of pivotal movement between the shank 27 and the receiver 28. Polyaxial bone screws with other types of capture connections may also be used according to the invention, including but not limited to, threaded connections, frictional connections utilizing frustoconical or polyhedral capture structures, integral top or downloadable shanks, and the like. Also, as indicated above, polyaxial and other bone screws for use with connecting members of the invention may have bone screw shanks that attach directly to the connecting member or may include compression members or inserts, such as the members 29 and 30 that engage the bone screw shank and cooperate with the shank, the receiver and the closure structure to secure the connecting member assembly to the bone screw and/or fix the bone screw shank at a desired angle with respect to the bone screw receiver that holds the longitudinal connecting member assembly. Furthermore, although the closure structure 32 of the present invention is illustrated with the polyaxial bone screw 25 having an open receiver or head 28, it foreseen that a variety of closure structures may be used in conjunction with any type of medical implant having an open or closed head or receiver, including monoaxial bone screws, hinged bone screws, hooks and the like used in spinal surgery.

To provide a biologically active interface with the bone, the threaded shank 27 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding. It is also foreseen that combinations of the above can be used, such as a composite of titanium plasma spray and hydroxyapatite.

The closure structure 32 can be any of a variety of different types of closure structures for use in conjunction with the present invention with suitable mating structure on the interior surface of the upstanding arms of the receiver 28. The illustrated closure structure 27 is in two pieces with the outer fastener 33 rotatable between the spaced arms and the inner set screw 34 rotatable within the outer fastener 33. However, single piece closures may be used and other structures, such as slide-in closure structures may be used as an alternative to helically wound closures. The illustrated outer fastener 33 is substantially cylindrical and includes an outer helically wound guide and advancement structure in the form of a flange form that may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure downward between the receiver arms and having such a nature as to resist splaying of the arms when the closure structure is advanced into the U-shaped channel formed by the arms. The illustrated closure 32 further includes the inner set screw 34 with an internal drive in the form of an aperture utilized for assembly of the set screw and removal of the entire closure 32. It is foreseen that the closure structure may alternatively include an external drive, such as a break-off head designed to allow such a head to break from a base of the closure at a preselected torque, for example, 60 to 120 inch pounds. Such a closure structure would also include a base having an internal drive to be used for closure removal.

Returning to the longitudinal connecting member assembly 1 illustrated in FIGS. 1-37, the assembly 1 is elongate, with the inner core 6 being a substantially solid, smooth and in the form of a uniform cylinder or rod having an outer cylindrical surface 36 and a substantially circular cross-section. The core 6 and integral anchor attachment portion 8 may be made from metal, metal alloys or other suitable materials, including plastic polymers such as polyetheretherketone (PEEK), ultra-high-molecular weight-polyethylene (UH-MWP), polyurethanes and composites, including composites containing carbon fiber and layers of different materials. It is noted that although an anchor member 4 is illustrated in which the components 6 and 8 are integral, the core 6 and the anchor attachment portion 8 may be made from different materials, for example, the core 6 may be made out of PEEK and inserted into and fixed and/or adhered to a bone anchor attachment portion 8 made out of titanium. The core 6 and attachment portion 8 may include a small central lumen or through-bore (not shown) extending along the central axis A. Such a lumen may be used as a passage through the entire assembly 1 interior for a length of a guide wire for aiding insertion of the assembly 1 between implanted bone screws 25 in a percutaneous or less invasive procedure.

With particular reference to FIGS. 3 and 5, the anchor member 4 is substantially cylindrical along an entire length thereof along the axis A and includes at least two or more circular cross-sections along the length thereof. The illustrated member 4 includes the slender and thus more flexible core 6 of a first circular cross-section and the bone anchor attachment portion 8 that has a second circular cross-section that is larger than the core 6 cross-section and thus is more rigid than the core 6. The core 6 terminates at an end 38. Prior to final assembly by the vendor or manufacturer, the core 6 is typically of a length greater than that shown in the drawing figures so that the core 6 may be grasped by a tool (not shown) near the end 38 and pulled along the axis A in a direction away from the anchor attachment portion 8, in certain embodiments, tensioning the core 6 and putting compressive forces on the spacers and bumper, as will be described in greater detail below. Between the core 6 and the portion 8 is a buttress plate or annular enlargement 40 that has a third circular cross-section that is larger than the attachment portion 8 cross-section. The buttress plate 40 is integral with and disposed between the core 6 and the portion 8. Although the illustrated anchor member 4 is substantially cylindrical, it is foreseen that the core 6, the portion 8 and the plate 40 may have other forms, including but not limited to oval, square and rectangular cross-sections as well as other curved or polygonal shapes. The bone anchor attachment portion 8 is of a length along the axis A for cooperating with at least one and up to a plurality of bone attachment members, such as the bone screws 25, hooks or other types of bone anchors. The portion 8 is substantially solid and rigid, with an outer cylindrical surface 39 that terminates at an end 41. The plate 40 includes a first substantially flat and annular face 42 facing away from the core 6 and an opposed face 44 facing toward the core 6. The faces 42 and 44 extend radially from the axis A. An outer cylindrical surface 46 extends between the faces 42 and 44. A gently sloping transition surface or flange 48 bridges between and connects the outer cylindrical surface 36 of the core 6 with the substantially flat facing face 44 of the buttress plate 40.

With particular reference to FIGS. 13-15 and 19-22, the sleeves 12 and 16 are each sized and shaped to be slidingly received over the core 6 along the axis A and each have a length measured along the axis A that is sufficient for the attachment of at least one bone screw 25 thereon. Similar to the inelastic anchor member 4, the inelastic sleeves 12 and 16 may be made from metal, metal alloys or other suitable materials, including plastic polymers such as polyetheretherketone (PEEK), ultra-high-molecular weight-polyethylene (UHMWP), polyurethanes and composites, including composites containing carbon fiber. The sleeves 12 and 16 may be made of the same material as the cooperating core 6, for example, the anchor member 4 and the sleeves 12 and 16 may all be made from PEEK; or, for example, the core 6 may be made from one material, such as PEEK, while the sleeves 12 and 16 may be made from another material, such as a metal (e.g. stainless steel or titanium). In order to have low or no wear debris, the sleeve 12 and 16 inner surfaces and/or cooperating core 6 outer surfaces may be coated with an ultra thin, ultra hard, ultra slick and ultra smooth coating, such as may be obtained from ion bonding techniques and/or other gas or chemical treatments.

The illustrated sleeves 12 and 16 each are substantially cylindrical, having outer cylindrical bone anchor attachment surfaces 50 and 52, respectively, that are each of substantially the same diameter as the outer surface 39 of the bone anchor attachment portion 8. Each of the sleeves 12 and 16 further include a substantially cylindrical inner surface 54 and 56, respectively, that define a through-bore for the passage of the core 6 therethrough. While the surface 56 is shown as being cylindrical, the illustrated surface 54 of the sleeve 12 is preferably curved and shown as slightly hour-glass or hyperboloid-like in configuration running along the axis A, and/or at least has non-linear relief at one or both ends. The slightly curved surface 54 results in at least a partially non-linear inner lumen that decreases both bending stresses along the core 6 and wear debris between the parts. For example, if the core 6 is flexed, the inner surface 54 allows deformation of the core over a longer area or length resulting in reduced stresses and a longer fatigue life. Furthermore, if the core 6 is made from a material such as PEEK, the curved surface 54 and/or end surface non-linear relief reduces contact wear and bending stresses along the core 6 surface that is received by the sleeve 12. The sleeve 12 includes a pair of opposed end plates 58 and 60 and the sleeve 16 includes a pair of opposed end plates 62 and 63. The illustrated plates 58, 60, 62 and 63 have outer cylindrical surfaces 64, 66, 68 and 69, respectively, that are of substantially the same diameter as the buttress plate outer cylindrical surface 46. The sleeve 12 includes opposed curved and slightly concave flanged end surfaces 70 and 72, each running from the inner surface 54 radially outwardly toward respective cylindrical surfaces 64 and 66. The illustrated concave surfaces 70 and 72 are partially spherical. The sleeve 16 includes one concave end surface 74 and an opposed planar end surface 76. The illustrated surface 74 is partially spherical.

With reference to FIGS. 6-9, 16-18 and 23-25, the elastic spacers 10 and 14 and the elastic bumper 18 are sized and shaped to be slidingly received over the core 6 and may be made from a variety of elastic materials of different durometers and materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacers 10 and 14 and bumper 18 inner and side surfaces may also be coated with an ultra thin, ultra hard, ultra slick and ultra smooth coating, such as may be obtained from ion bonding techniques and/or other gas or chemical treatments.

The illustrated spacers 10 and 14 advantageously cooperate with the core 6 of the anchor member 4, providing directed axial movement, limitation and protection of movement by the sleeves 12 and 16 along the core 6 located between bone screws 25. With particular reference to FIGS. 6-9 and 16-18, the illustrated spacers 10 and 14 are substantially similar in geometry, differing only with regard to inner surfaces that define through bores for receiving the anchor member core 6 and number of optional outer grooves. Each of the spacers 10 and 14 have an external substantially cylindrical outer surface 78 and 80, respectively, and internal surfaces 82 and 84, respectively, each defining through bores. The internal surface 82 is further defined by a flared or conical outwardly extending surface 86 sized and shaped for cooperating with the transition surface 48 of the anchor member 4. The spacer 10 includes opposed substantially planar and annular end surfaces 88 and 89 and the spacer 14 includes opposed substantially planar and annular end surfaces 90 and 91. When cooperating with the core 6, the end surfaces 88 and 89 and 90 and 91 are substantially perpendicular to the axis A. It is foreseen that in some embodiments, the spacers 10 and 14 may be of circular, square, rectangular or other cross-section including curved or polygonal shapes. In the illustrated embodiment, both the spacers 10 and 14 further include optional compression grooves, the spacer 10 having a single groove 93 and the spacer 14 having a pair of grooves 94 and 95. Spacers according to the invention may include one, none or any desired number of grooves that allow for some additional compression of the spacers 10 and 14 when pressed upon in an axial direction between the bone anchor attachment portion 8 and the cooperating sleeves 12 and 16. The illustrated groove 93 and groove pair 94 and 95 are substantially uniform and circular in cross-section, being formed in the respective external surfaces 78 and 80 and extending radially toward respective internal surfaces 82 and 84. The size of the internal surfaces 82 and 84 allow for some axially directed sliding movement of the respective spacers 10 and 14 with respect to the core surface 36. The illustrated spacer 14 is more elastic than the spacer 10, both with respect to geometry, by having more grooves than the spacer 10 and also may be made from a material with greater elasticity (lower durometer) than the spacer 14, resulting in an assembly that advantageously provides for greater travel of the assembly in a cephalad direction, if desired.

Figure 10:
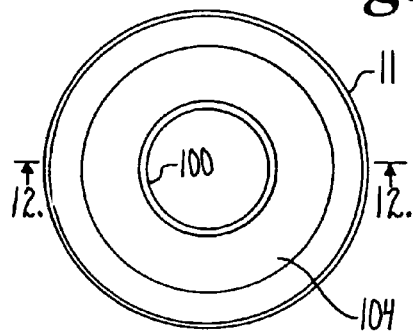
FIG. 10 is an enlarged top plan view of the first pressure washer of FIG. 3.
Figure 11:
FIG. 11 is an enlarged side elevational view of the first pressure washer of FIG. 3.
Figure 12:
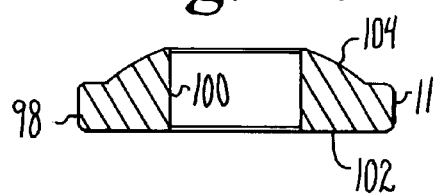
FIG. 12 is an enlarged cross-sectional view taken along the line 12-12 of FIG. 10.
Figure 14:
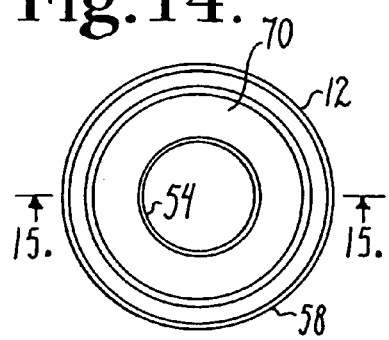
FIG. 14 is an enlarged top plan view of the first sleeve of FIG. 3.
Figure 13:
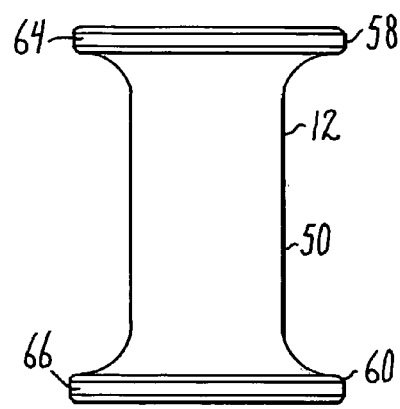
FIG. 13 is an enlarged side elevational view of the first sleeve of FIG. 3.
Figure 15:
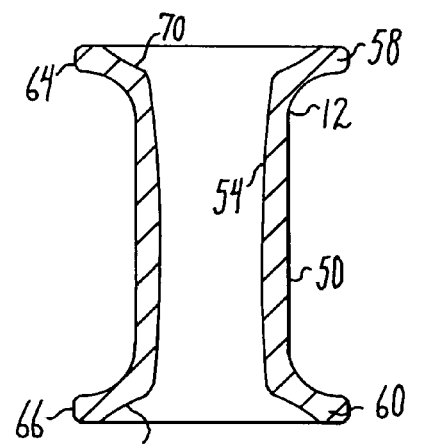
FIG. 15 is an enlarged cross-sectional view taken along the line 15-15 of FIG. 14.
Figure 16:
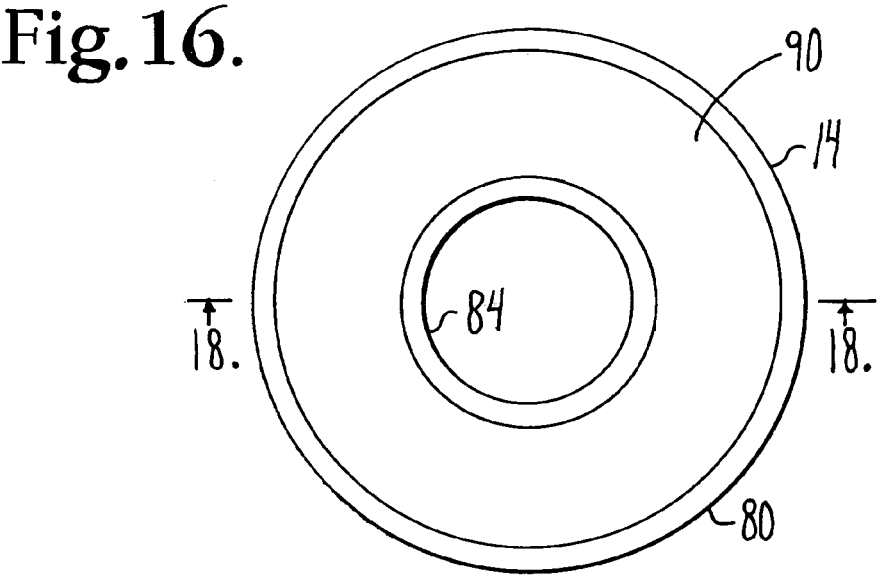
FIG. 16 is an enlarged top plan view of the second spacer of FIG. 3.
Figure 17:
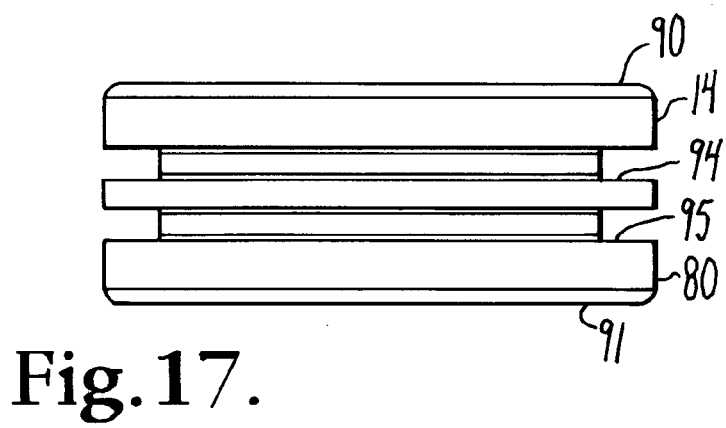
FIG. 17 is an enlarged side elevational view of the second spacer of FIG. 3.
Figure 18:
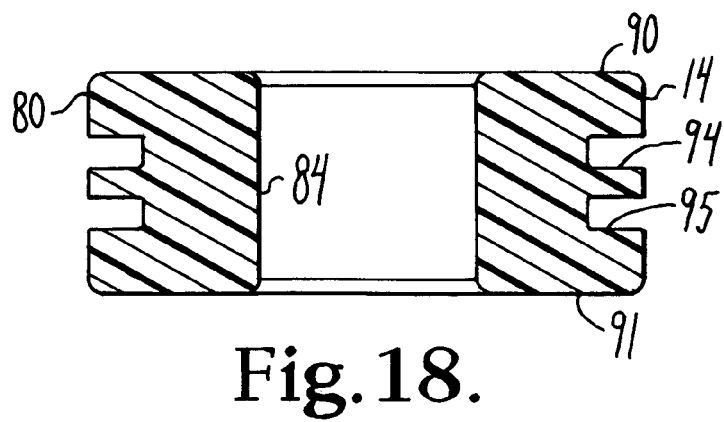
FIG. 18 is an enlarged cross-sectional view taken along the line 18-18 of FIG. 16.
Figure 19:
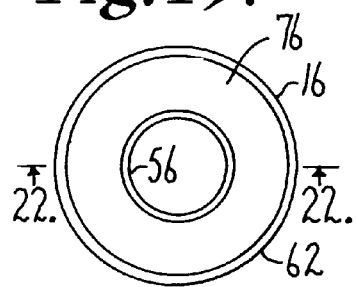
FIG. 19 is an enlarged top plan view of the second sleeve of FIG. 3.
Figure 20:
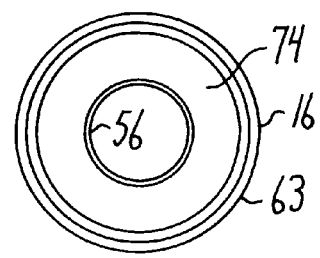
FIG. 20 is an enlarged bottom plan view of the second sleeve of FIG. 3.
Figure 21:
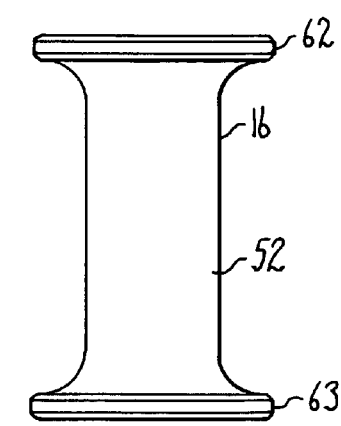
FIG. 21 is an enlarged side elevational view of the second sleeve of FIG. 3.
Figure 22:
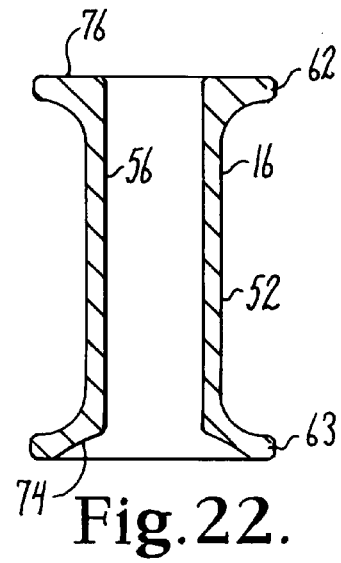
FIG. 22 is an enlarged cross-sectional view taken along the line 22-22 of FIG. 19.

With particular reference to FIGS. 10-12, the domed articulating wear or pressure washer 11 is shown. With reference to FIG. 3, for example, it is noted that the pressure washers 13 and 15 are identical to the illustrated pressure washer 11, thus the discussion herein of the pressure washer 11 also applies to the washers 13 and 15. The pressure washer 11 has an external substantially cylindrical outer surface 98 and internal substantially cylindrical surface 100, defining a through bore sized and shaped to receive the core 6. The washer 11 further includes a substantially planar end surface 102 and an opposed, curved, convex surface 104 sized and shaped for cooperation with a substantially concave surface of a cooperating sleeve, such as the surface 70, surface 72 or the surface 74. The illustrated convex surface 104 is at least partially spherical. When cooperating with the core 6, the end surface 102 is substantially perpendicular to the axis A. The size of the internal surface 100 allows for some axially directed sliding movement of the washer 11 with respect to the core surface 36. The washer 11 is preferably made from a firm material, such as metal and metal alloys with titanium being particularly preferred; or other suitable materials, including plastic polymers such as polyetheretherketone (PEEK), ultra-high-molecular weight-polyethylene (UH-MWP), polyurethanes and composites, including composites containing carbon fiber. In order to reduce wear debris, the washers 11, 13 and 15 are preferably made from a material different than the cooperating sleeves 12 and 16. For example, the sleeves 12 and 16 may be made of a titanium alloy while the washers 11, 13 and 15 may be made from a high molecular weight polyethylene. With particular reference to the washer 11 and as shown in FIG. 4, with the convex surface 104 slidingly engaging the concave surface 72 of the sleeve 12, the pressure washer 11 advantageously allows for tilt, slide and rotation of the washers along the core 6 and with respect to the sleeve 12, maintaining substantially full contact between the washer 11 and the sleeve 12, resulting in better load distribution along the assembly 1, keeping stresses on the inside of the tubular sleeve 12, rather than on an outer surface or end, and thus allowing for better angulation, translation and compression of the entire assembly 1, as each of the pressure washers 11, 13 and 15 have curved, convex surfaces fully contacting and cooperating with substantially similarly curved concave inner surfaces of the sleeves 12 and 16. Thus, the core 6, cooperating compressible spacers 10 and 14, sleeves 12 and 16 and washers 11, 13 and 15 allow for some twist or turn, providing some relief for torsional stresses.

Figure 33:
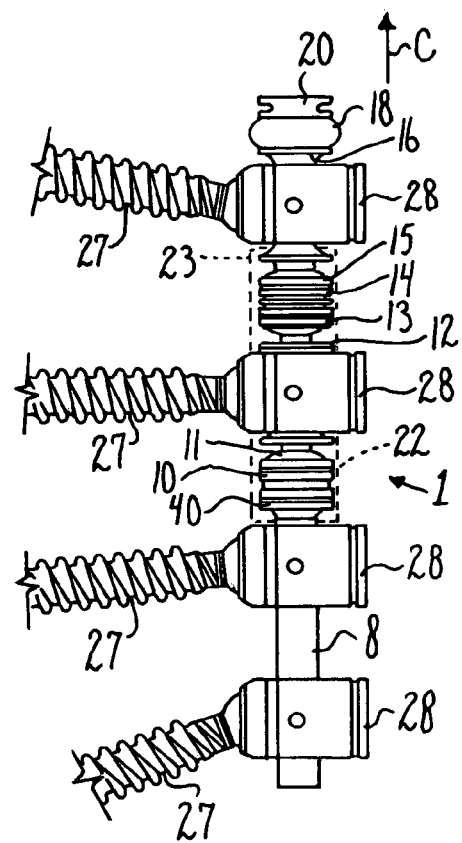
FIG. 33 is a partial side elevational view of the assembly of FIGS. 1 and 2 with optional over-molds shown in phantom and with differential displacement in a cephalad direction.

The over-molded coverings 22 and 23 are preferably thin, soft and elastic, primarily provide protection to the body by keeping wear debris within the assembly 1 and keeping scar tissue out of the assembly 1 at the juncture between the spacers, washers and sleeves. Particularly when the assembly 1 is placed in tension as shown in FIG. 33, the over-molded sections 22 and 23 provide a covering over the components that may separate, for example, the pressure washer 11 and the sleeve 12, guarding against gaps that might otherwise irritate scar and surrounding body tissue. The over-molded sections 22 and 23 may be made of a variety of materials including natural and synthetic plastics and composites. The illustrated over-molds 22 and 23 are a molded thermoplastic elastomer, for example, polyurethane or a polyurethane blend; however, any suitable polymer material may be used.

The illustrated over-mold 22 is fabricated around and about the surfaces 42 and 46 of the anchor plate 40, the entire spacer 10, the entire washer 11 and the entire end plate 60 of the sleeve 12. The illustrated over-mold 23 is fabricated around and about the surfaces of the end plate 58 of the sleeve 12, the entire washer 13, the entire spacer 14, the entire washer 15 and the entire end plate 63 of the sleeve 16. The over-molds 22 and 23 are fabricated from an initially flowing elastomer, as will be described more fully below, with the elastomer engaging and possibly adhering to the surfaces of the sleeves, washers and spacers being covered thereby. Each formed elastomer is substantially cylindrical, but thin so as to also be flexible and deformable when the assembly 1 is bent, compressed or stretched as shown in the drawing figures. In both spinal flexion and extension, the over-molds 22 and 23 completely surround or cover the assembly 1 components as also illustrated in the drawing figures. It is foreseen that the material for the over-molds 22 and 23 may be sized and made from such materials so as to provide for relatively more or less bendability, as well as compressibility and stretchability.

With particular reference to FIGS. 23-25, the elastic bumper 18 is substantially cylindrical, including an outer surface 108 and an inner surface 109 forming a substantially cylindrical through bore that opens at planar end surfaces 110 and 111 and operatively extends along the axis A. The bumper 18 may further include a compression groove or grooves similar in form and function to the compression grooves 93, 94 and 95 described above with respect to the spacers 10 and 14. The bumper 18 is sized and shaped to slidingly receive the core 6 through the inner surface 109. The bumper 18 is preferably made from an elastomeric material such as polyurethane, but may be made from any suitable elastomeric material. The bumper 18 is typically more elastic than either of the spacers 10 and 14, providing greater movement of the sleeve 16 in a direction toward the bumper 18 than toward the spacer 14.

With particular reference to FIGS. 26-28, the crimping ring 20 is substantially cylindrical and includes an outer surface 120 and an inner surface 122 forming a substantially cylindrical through bore that opens at planar end surfaces 124 and 126 and operatively extends along the axis A. The crimping ring 20 is sized and shaped to receive the elongate core 6 through the inner surface 122. The crimping ring 20 further includes a pair of opposed crimp or compression grooves 130 that are pressable and deformable inwardly toward the axis A upon pre-compression of the spacers 10 and 14 and the bumper 18 during assembly of the assembly 1. The crimping ring 20 is preferably made from a stiff, but deformable material, including metals and metal alloys. As an alternative to the grooves 130, in certain embodiments of the invention, the crimp ring 20 may include an inner helical thread (not shown) with the core 6 having a mating helical outer thread (not shown), for fixing the ring 20 on the core 6 and compressing the spacers 10 and 14 and bumper 18 to a desired degree.

The illustrated dynamic connecting member assembly 1 having pre-compressed spacers is shown cooperating with four polyaxial bone screws 25 as shown in FIG. 2. In use, the bone screws 25 are implanted into vertebrae (not shown). Each vertebra may be pre-drilled to minimize stressing the bone. Furthermore, when a cannulated bone screw shank is utilized, each vertebra will have a guide wire or pin inserted therein that is shaped for the bone screw cannula of the bone screw shank 27 and provides a guide for the placement and angle of the shank 27 with respect to the cooperating vertebra. A further tap hole may be made and the shank 27 is then driven into the vertebra by rotation of a driving tool (not shown) that engages a driving feature on or near a top portion of the shank 27. It is foreseen that both the screws 25 and the longitudinal connecting member assembly 1 may be inserted in a conventional, percutaneous or other minimally invasive surgical manner.

Figure 32:
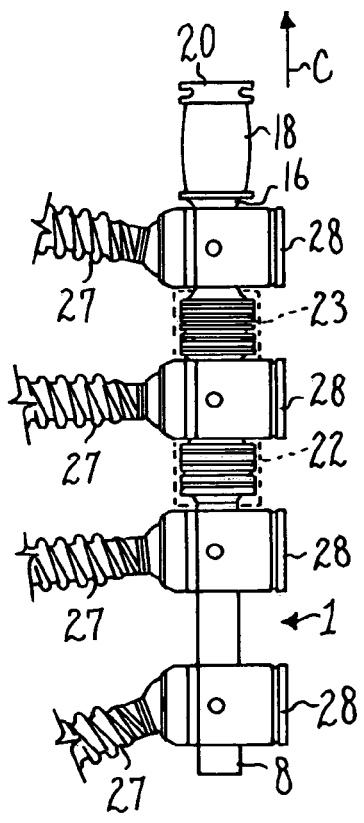
FIG. 32 is a partial side elevational view of the assembly of FIGS. 1 and 2 with optional over-molds shown in phantom and with differential displacement in a caudal direction.

With particular reference to FIGS. 1-4, the longitudinal connecting member assembly 1 is assembled to provide pre-compressed spacers 10 and 14 and bumper 18 prior to implanting the assembly 1 in a patient. FIGS. 1, 2 and 4 illustrated the pre-compressed, ready to use assembly 1, while FIG. 32 illustrates the assembly 1 during spinal movement that results in further compression of the spacers 10 and 14, while FIG. 33 illustrates the assembly 1 during spinal movement that results in further compression of the bumper 18 and extension of the assembly 1 at the spacers 10 and 14. With particular reference to FIG. 3, the assembly 1 is assembled by first providing the anchor member 4 that has a core 6 that is longer in the axial direction A than the core 6 illustrated in the drawing figures. The spacer 10 is first loaded onto the core 6 by inserting the core 6 end 38 into the bore defined by the inner surface 82 with the face 89 directed toward the buttress plate 40. The spacer 10 is moved along the core 6 until the surface 86 contacts the surface 48. The pressure washer 11 is then threaded on the core 6 with the face 102 facing the end surface 88 of the spacer 10. The sleeve 12 is then threaded onto the core 6 with the concave face 72 of the plate 60 facing the convex surface 104 of the pressure washer 11. The core 6 is then received in the bore of the pressure washer 13, with the convex face of the washer 13 facing the concave face 70 of the sleeve 12. The spacer 14 is thereafter loaded onto the core 6 by inserting the core 6 end 38 into the bore defined by the inner surface 84 with the face 91 facing the toward the pressure washer 13. The spacer 14 is moved along the core 6 until the spacer 14 contacts the pressure washer 13. The pressure washer 15 is then threaded on the core with a planar face thereof facing the planar face 90 of the spacer 14. The sleeve 16 is then threaded onto the core 6 with the concave face 74 facing the convex end surface of the pressure washer 15. The core 6 is received in the bore defined by the inner cylindrical surface 56 and the sleeve 16 is moved along the core 6 until the sleeve 16 abuts the pressure washer 15. The bumper 18 is thereafter loaded onto the core 6 by inserting the core 6 end 38 into the bore defined by the inner surface 109 with the face 111 facing the toward the planar end surface 76 of the sleeve 16. The bumper 18 is moved along the core 6 until the surface 111 contacts the surface 76. The crimping ring 20 is thereafter loaded onto the core 6 by inserting the core 6 end 38 into the bore defined by the inner surface 122 with the face 126 facing the toward the surface 110 of the bumper 18. The crimping ring 20 is moved along the core 6 until the surface 126 contacts the surface 110. It is noted that due to the symmetrical nature of the sleeve 12, the spacer 14, the bumper 18 and the crimping ring 20, these components may be loaded onto the core 6 from either side thereof.

After the crimping ring 20 is loaded onto the core 6, manipulation tools (not shown) are used to grasp the core 6 near the end 38 and at the bone anchor attachment portion 8, placing some tension on the core 6. The spacer 10, the sleeve 12, the spacer 14, the sleeve 16, the bumper 18 and the crimping ring 20 are moved toward the buttress plate 40 and into contact with one another. A desired amount of axial compressive force is placed on the components loaded on the core 6, followed by deforming the crimping ring at the crimp grooves 120 and against the core 6. When the manipulation tools are released, the crimping ring 20, now firmly and fixedly attached to the core 6 holds the spacers 10 and 14 and the bumper 18 in compression and the spacers and bumper place axial tension forces on the core 6, resulting in a dynamic relationship between the core 6 and the spacers 10, 14 and the bumper 18. The spacers 10 and 16 are slidable with respect to the core 6, but also are limited by the buttress plate of the anchor member 4 and end plates of the sleeves 12 and 16. Furthermore, the bumper 18 that is compressed between the sleeve surface 76 and the crimping ring surface 116 is also slidable with respect to the core 6. The spacers 10 and 14 and the bumper 18 place a distractive force on the core 6 along the axis A and between the buttress plate 40 and the crimping ring 20, but also are movable with respect to the core 6, thus being able to respond to jolting and other body movements and thereafter spring back into an originally set location. The sleeves 12 and 16 that may compress slightly, but are more rigid than the spacers 10 and 14, keep the spacers 10 and 14 in an approximate desired axially spaced relation. However, the spacers 10 and 14 also advantageously slide along the core 6 in response to outside forces. The core 6 is then trimmed to be approximately flush with the end surface 114 of the crimping ring 20.

It is noted that mechanical characteristics of the assembly components, such as creep, may require the spacers 10 and 14 and the bumper 18 to be compressed at a higher load and then allowed to reach a steady state before placement and molding of the over-mold coverings 22 and 23 and eventual operative use with the bone screws 25. The over-molds 22 and 23 are fabricated by first placing the anchor portion 8 and/or the sleeves 12 or 16 in a jig or other holding mechanism such that the jig frictionally engages such portion 8 and/or sleeves 12 and 16, followed by fabricating the over-mold 22 about and between the plate 40, the spacer 10, the pressure washer 11 and an end portion of the sleeve 12 and the over-mold 23 about and between an opposite end portion of the sleeve 12, the washer 13, the spacer 14, the washer 15 and an end portion of the sleeve 16 as best shown in phantom in FIG. 4. In a preferred method of fabrication of the over-molds 22 and 23, an elastic, polymeric material flows about the desired components of the assembly 1 at room temperature, followed by a vacuum cure. It is noted that in some embodiments of the invention, the over-molds 22 and 23 may be fabricated about the desired assembly 1 components prior to compression of the spacers 10 and 14 and the bumper 18. In other embodiments, the over-molds 22 and 23 may be fabricated about the spacers 10 and 14 after an initial compression of the spacers, followed by a final compression step after cure of the over-molds.

With reference to FIGS. 2 and 29-37, the assembly 1 is eventually positioned in an open or percutaneous manner in cooperation with the bone screws 25 with the over-molds 22 and 23 disposed between bone screws 25, with a bone screw attached to each of the sleeves 12 and 16 and, as illustrated, two bone screws 25 attached to the anchor portion 8. A closure structure 32 is used to attach each screw 25 to the assembly 1 with the sleeves 12 and 16 and the anchor portion 8 each being cradled between a lower pressure insert 29 and an upper pressure insert 30.

With particular reference to FIGS. 2, 32-33, a desired placement of the assembly 1 is shown wherein an arrow C indicates movement of the bone screws 25 attached to the sleeves 12 and 15 generally in a cephalad or cranial direction. Specifically, FIG. 2 illustrated a pre-compressed assembly 1 in a neutral position, FIG. 32 illustrates compression of the spacers 10,14 and FIG. 33 shows extension or tension of the assembly at spacers 10,14 and movement of the sleeves 12 and 16 in a cephalad direction (arrow c). FIGS. 32-33 illustrate how the assembly 1 allows greater movement of the sleeves and thus the bone screws 25 and attached spinal segments in the cephalad direction than in the caudad direction, the elastic bumper 18 being the most compressible component of the assembly 1 and the spacer 14 being more elastic and thus more compressible than the spacer 10 due to the geometry thereof (e.g., an extra groove in the spacer 14). In other embodiments of the invention, the spacer 14 may be made from a material of different durometer than the spacer 10, to allow for a desirable increased upward or cephalad movement of a portion of the assembly 10.

Figure 34:
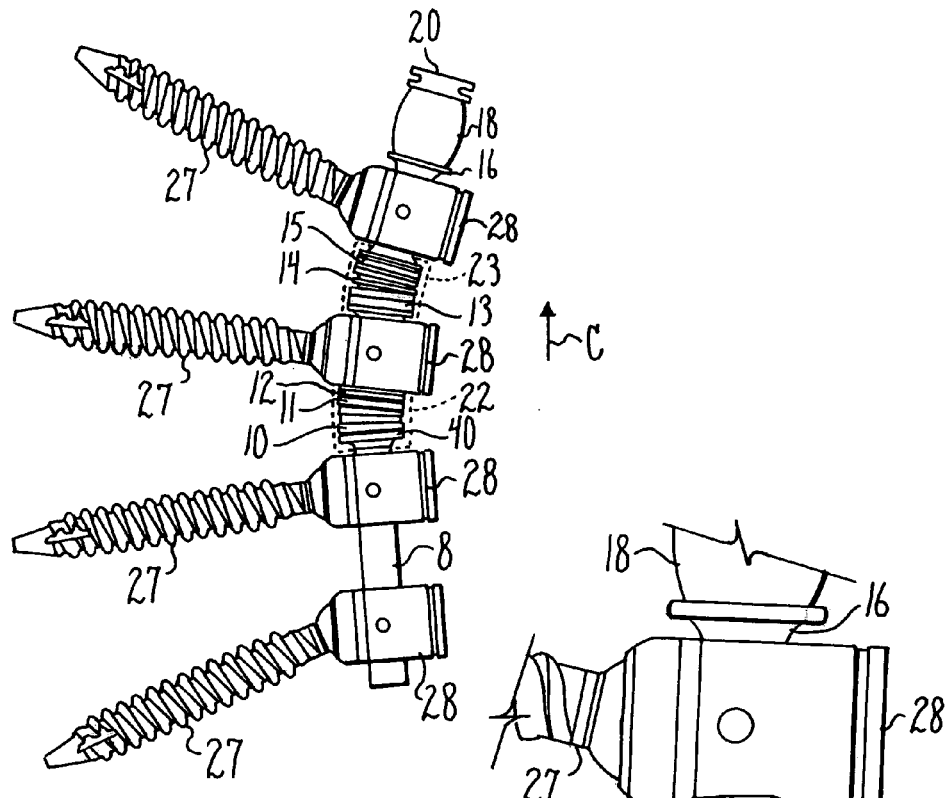
FIG. 34 is a side elevational view of the assembly of FIGS. 1 and 2 with optional over-molds shown in phantom and shown operatively responding to spinal extension or lordosis.
Figure 35:
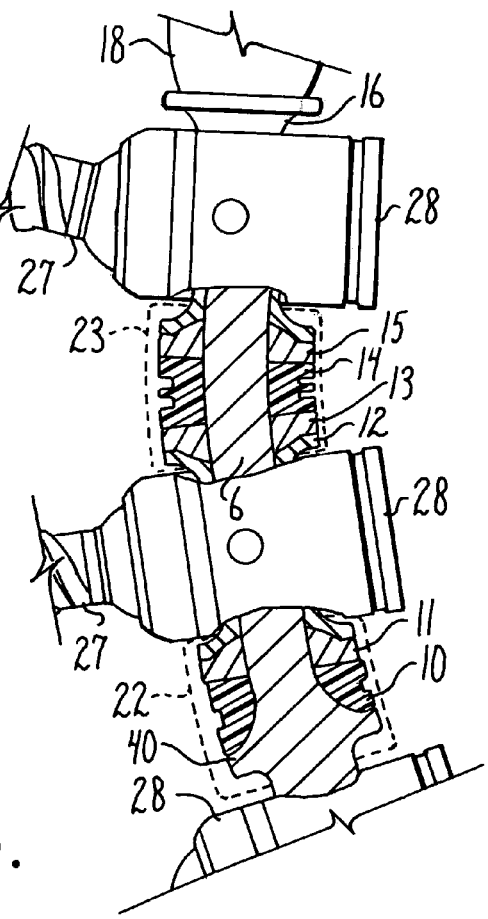
FIG. 35 is an enlarged and partial side elevational view, similar to FIG. 34 with portions broken away to show the detail thereof.
Figure 36:
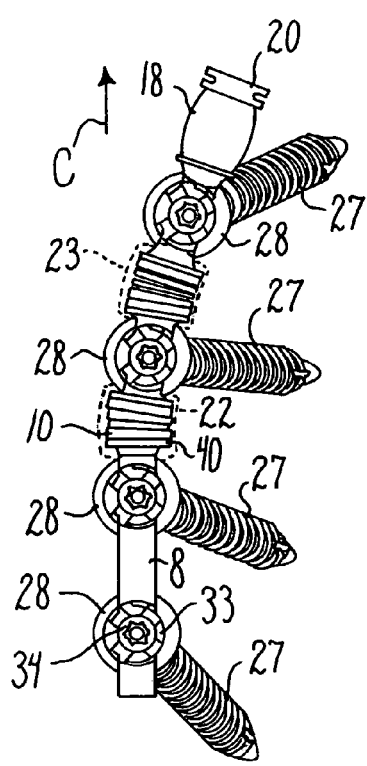
FIG. 36 is a rear elevational view of the assembly of FIGS. 1 and 2 with optional over-molds shown in phantom and shown operatively responding to spinal scoliosis.
Figure 37:
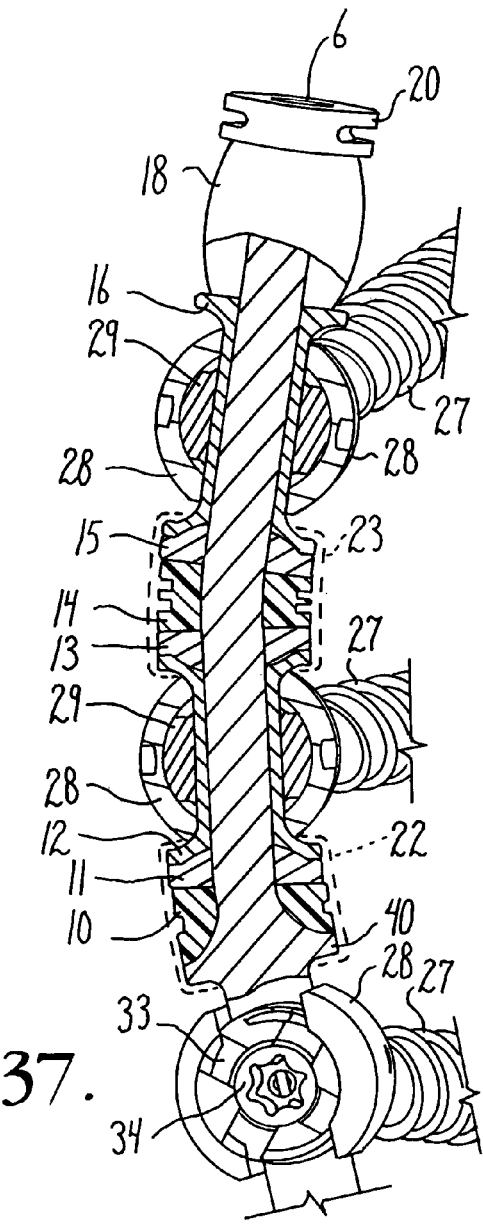
FIG. 37 is an enlarged and partial rear elevational view, similar to FIG. 36 with portions broken away to show the detail thereof.

With reference to FIGS. 34 and 35, supported spinal extension as well as movement in the cephalad direction C is also possible with the assembly 1. The washers 11, 13 and 15 are slidable and rotatable with respect to the cooperating sleeves 12 and 16, advantageously providing steady, balanced and controlled load distribution during angulation, both spinal extension and flexion as well as during compression and tension. Furthermore, the washers 11, 13, and 15 and sleeves 12 and 16 cooperate with the spacers 10 and 14 to aid in bending and tilting of the assembly 1, supporting and controlling the spine in response to lordosis and kyphosis, for example, and also providing for rotation and tilting of the assembly in both coronal and sagittal planes, supporting and controlling the spine in the case of scoliosis as shown in FIGS. 36 and 37. Thus, once attached to the bone screws 25, the assembly 1 is substantially dynamically loaded and oriented relative to the cooperating vertebra, providing relief (e.g., shock absorption) and protected movement with respect to not only flexion and extension, but also to distractive, compressive, torsional and shear forces placed on assembly 1 and bone screws 25.

If removal of the assembly 1 from any of the bone screw assemblies 25 is necessary, or if it is desired to release the assembly 1 at a particular location, disassembly is accomplished by using a driving tool (not shown) with a driving formation cooperating with the closure structure 32 to rotate and remove the closure structure from the receiver 28. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the rod portions 8, utilizing the same bone screw 25 components. Alternatively, if less support is eventually required, a less rigid, more flexible assembly, for example, an assembly 1 made with elastic spacers and bumper of different durometer or geometry may replace the assembly 1, also utilizing the same bone screws 25.

Figures 38, 39:
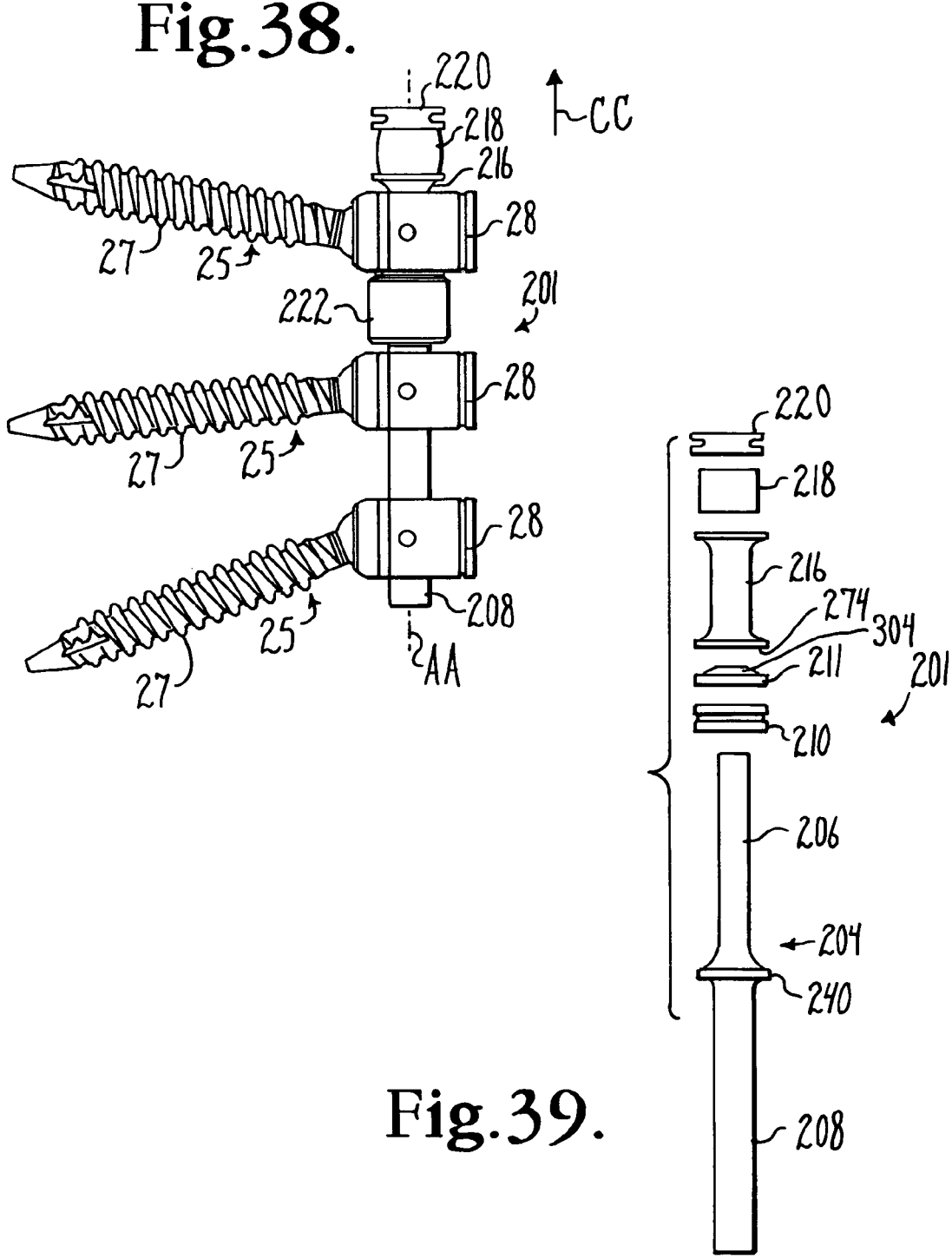
FIG. 38 is an enlarged side elevational view of a second embodiment of a dynamic connecting member assembly according to the invention shown with three bone screws.
FIG. 39 is an enlarged and exploded side elevational view of the assembly of FIG. 38.
Figure 40:
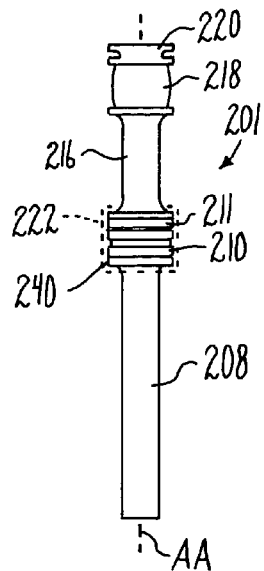
FIG. 40 is an enlarged side elevational view of the assembly of FIG. 38 with the optional over-mold in phantom.

With reference to FIGS. 38-44, an alternative embodiment of a dynamic longitudinal connecting member, generally 201 is substantially similar to the assembly 1 with the exception that it is shorter than the assembly 1, cooperating with fewer bone screws along an elastic and more flexible portion thereof. Similar to the assembly 1, the assembly 201 provides for greater movement in the cephalad direction as indicated by the arrow marked CC. The assembly 201 includes an anchor member, generally 204, having an elongate segment or inner core 206 and a bone anchor attachment portion 208; an elastic spacer 210; a pressure washer 211; a sleeve 216; an elastic bumper 218; and a crimping ring 220; all substantially symmetrically aligned with respect to a central axis AA of the anchor member 204. The elongate core 206 of the anchor member 204 is receivable within the spacer 210, the washer 211, the sleeve 216, the bumper 218 and the crimping ring 220. Thus, the axis AA of the anchor member 204 is also the axis of the fully assembled assembly 201. When fully assembled and fixed with all components fixed in position, the spacer 210 and the bumper 218 are placed in compression as shown in FIG. 40 and an elastic over-mold or covering 222 is applied about a buttress plate 240 of the anchor 204, the spacer 210, the washer 211 and a portion of the sleeve 212 (the covering 222 shown in phantom in FIG. 40) prior to attachment to three bone screws 25 as shown in FIG. 38.

In the illustrated embodiment, the anchor member 204 is substantially similar to the anchor member 4 previously described herein with respect to the assembly 1. Therefore, the member 204 includes the core 206, the bone anchor attachment portion 208 and the integral buttress plate 240 identical or substantially similar in size and shape to the respective core 6, attachment portion 8 and buttress plate 40 of the anchor member 4 previously described herein. The member 204 differs from the member 4 only in that the length of the core 206 is shorter than the core 6 as the core 206 holds only one sleeve 216, one cooperating spacer 210 and one washer 211 as compared to the core 6 that holds two sleeves, two spacers and three cooperating washers. The spacer 210 is identical or substantially similar to the spacer 10 previously described herein. The sleeve 216 is identical or substantially similar to the sleeve 16, having a concave end surface 274 identical or substantially similar to the concave end surface 74 of the sleeve 16 previously described herein. The washer 211 is identical or substantially similar to the washer 11 previously described herein, having a substantially convex end surface 304 identical or substantially similar to the end surface 104 of the washer 11. The surface 304 is slidably engageable with the concave surface 274 of the sleeve 216 such that a full and even surface contact occurs between the sleeve 216 and the washer 211, providing better load distribution along the assembly 201, keeping stresses on the inside of the sleeve 216 rather than on an outer surface during angulation, translation and compression. The bumper 218 and the crimping ring 220 are identical or substantially similar to the respective bumper 18 and the crimping ring 20 previously described herein with respect to the assembly 1.

The assembly 201 is assembled in a manner substantially similar to the manner of assembly previously described herein with respect to the assembly 1, the assembly 201 however, does not include a second spacer or second sleeve. Therefore, the core 206 is first received within a through bore of the spacer 210, followed by the washer 211, then within an inner surface of the sleeve 216, followed by an inner through bore of the bumper 218 and then an inner through bore of the crimping ring 220. Similar to what has been described previously with respect to the assembly 1, the core 206 may initially be of a longer length measured along the axis AA than is shown in the drawing figures, allowing for a manipulation tool to grasp the core 206 near an end thereof that extends through the crimping ring bore. The spacer 210 and bumper 220 are compressed, followed by deformation of the crimping ring 220 against the core 206. Then, the covering 222 is fabricated about the plate 240, the spacer 210, the washer 211 and an end portion of the sleeve 216. The assembly is now in dynamic relationship with the spacer 210, washer 211, sleeve 216 and bumper 218 being slidable with respect to the core 206, the sleeve 216 being more readily movable in a direction toward the bumper 218 due to the greater elasticity of the bumper 218 as compared to the spacer 210.

The assembly 201 may then be implanted, cooperating with three bone screws 25 as illustrated in FIG. 38 and as previously described herein with respect to the assembly 1. Unlike the assembly 1 that provides for a more dynamic and flexible connection between three illustrated bone screws 25, the assembly 201 provides for dynamic stabilization between first and second bone screws 25 and a more rigid connection between the second bone screw 25 and a third bone screw 25 as both the second and third bone screws are attached to the rigid attachment portion 208.

Figure 41:
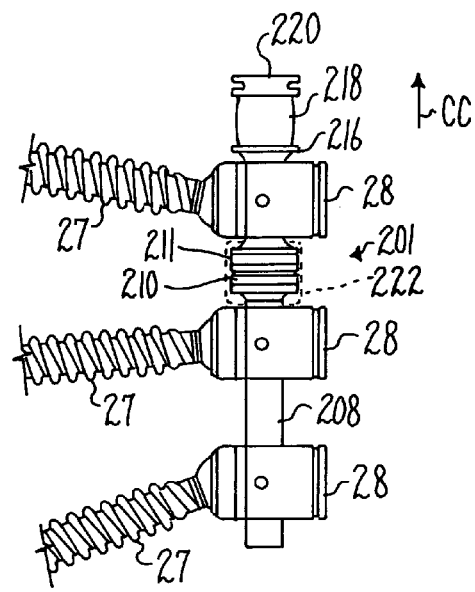
FIG. 41 is an enlarged and partial side elevational view of the assembly of FIG. 38 with the optional over-mold shown in phantom and the spacer shown under operative compression.
Figure 42:
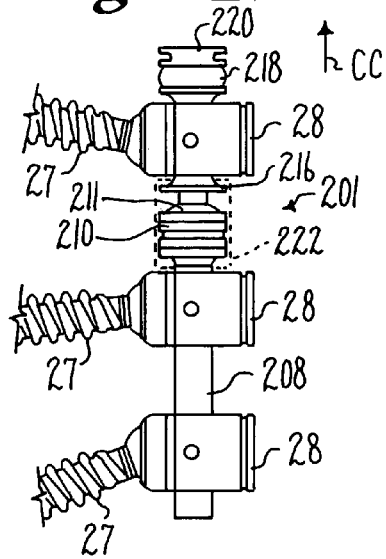
FIG. 42 is a partial side elevational view of the assembly of FIG. 38 with the optional over-mold shown in phantom and differential displacement in a cephalad direction in response to spinal distraction or tension.

FIGS. 41 and 42 illustrate a range of axial or spinal movement of the assembly in a cephalad direction as noted by the arrow CC. FIG. 41 shows the spacer 210 being compressed and thus the sleeve 216 and attached bone screw 25 moving in a caudal direction. FIG. 42 shows the bumper 218 in a fully compressed state with the sleeve 216 and attached bone screw 25 moving in a cephalad direction. As illustrated in FIG. 42, the optional over-mold 222 covers the portion of the assembly 201 that is being stretched and tensioned, covering a gap formed between the sleeve 216 and the pressure washer 211, protecting spinal tissue and retaining any wear debris within the assembly 201.

Figure 43:
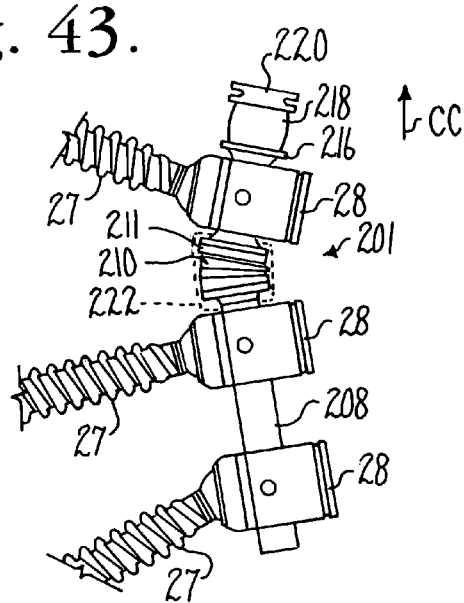
FIG. 43 is a side elevational view of the assembly of FIG. 38 with the optional over-mold shown in phantom and shown in compression and operatively responding to spinal extension or lordosis.

With reference to FIG. 43, the assembly 201 is shown in an angulated or bent position as it would be in response to spinal extension, for example. The load on the assembly 201 being stabilized by movement of the pressure washer 211 with respect to the sleeve 216 and also by partial compression of the spacer 210 along a groove thereof.

Figure 44:
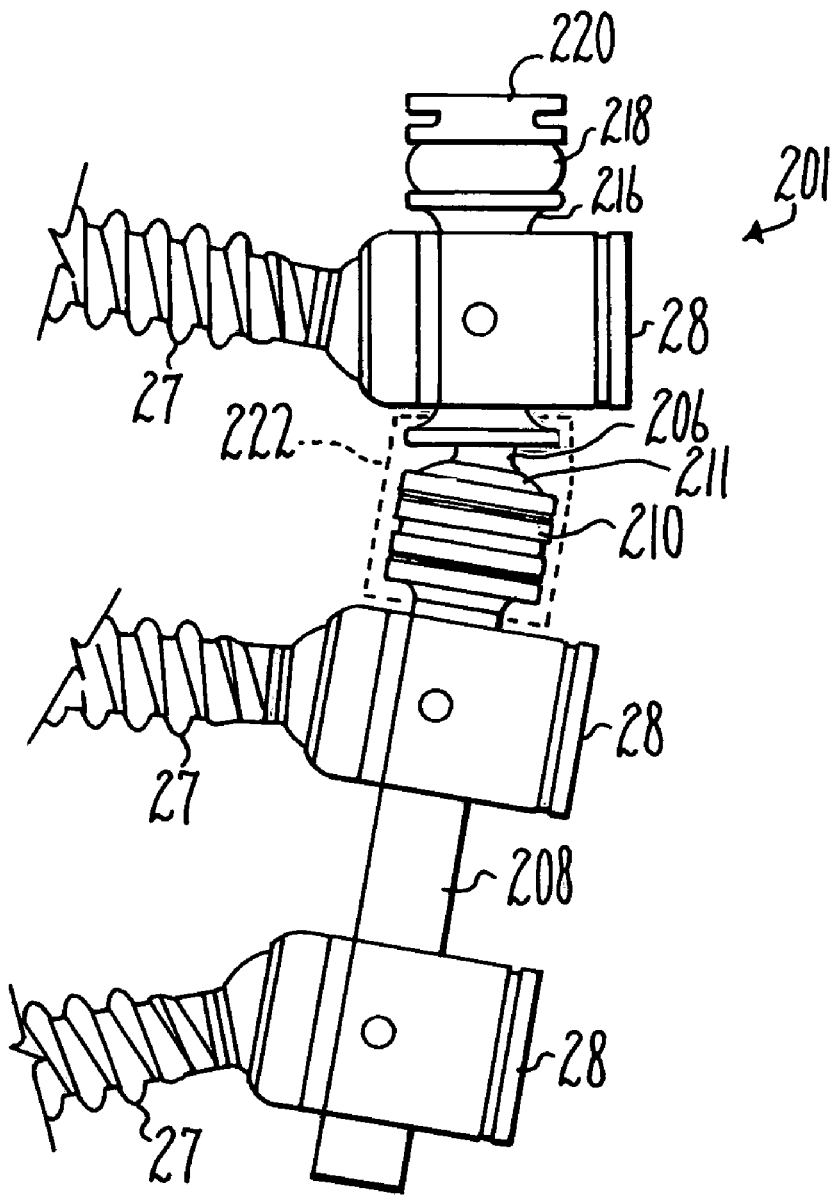
FIG. 44 is an enlarged side elevational view of the assembly of FIG. 38 with the optional over-mold shown in phantom and shown operatively responding to spinal distraction as well as flexion.

With reference to FIG. 44, the assembly 201 is shown in an angulated or bent position as it would be in response to spinal flexion, for example. The load on the assembly 201 is also distractive, causing a gap between the sleeve 216 and the pressure washer 211. The over-mold 222 advantageously stretches and prevents tissue from entering into the gap between the sleeve 216 and the washer 211.

Figure 47:
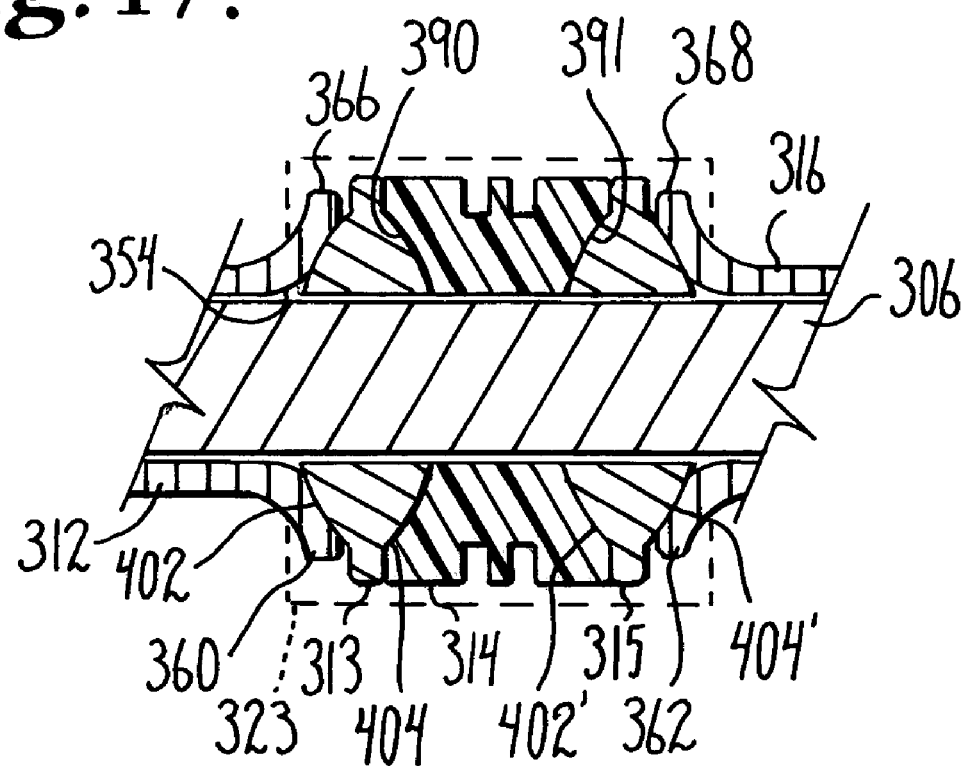
FIG. 47 is an enlarged and partial cross sectional view taken along the line 47-47 of FIG. 45 with an optional overmold shown in phantom.

With reference to FIGS. 45-47, an alternative embodiment of a dynamic longitudinal connecting member, generally 301 is substantially similar to the assembly 1 with the exception of some aspects of the geometry of the sleeve or tube trolley members, one of the spacers and two of the pressure washers located on either side of such spacer. Similar to the assembly 1, the assembly 301 provides for greater movement in the cephalad direction as indicated by the arrow marked CCC. The assembly 301 includes an anchor member, generally 304, having an elongate segment or inner core 306 and a bone anchor attachment portion 308; elastic spacers 310 and 314; pressure washers 311, 313 and 314; sleeves or tube trolleys 312 and 316; an elastic bumper 318; and a crimping ring 320, all substantially symmetrically aligned with respect to a central axis AAA of the anchor member 304. The elongate core 306 of the anchor member 304 is receivable within the spacers 310 and 314, the washers 311, 313 and 315, the sleeves 312 and 316, the bumper 318 and the crimping ring 320. Thus, the axis AAA of the anchor member 304 is also the axis of the fully assembled assembly 301. When fully assembled and fixed with all components fixed in position, the spacers 310 and 314 and the bumper 318 are placed in compression as shown in FIG. 45 and an optional elastic over-mold or covering, 322 is applied about a buttress plate 340 of the anchor 304, the spacer 310, the washer 311 and a portion of the sleeve 312 and an optional elastic over-mold or covering 323 is applied about a portion of the sleeve 312, the washer 313, the spacer 314, the washer 315 and a portion of the sleeve 316, both over-molds 322 and 323 molded over such component parts prior to attachment of the assembly 310 to three bone anchors such as the bone screws 25, in the same positions shown for the assembly 1 in FIG. 32, for example.

The anchor member 304, the spacer 310, the pressure washer 311, the sleeve 312, the bumper 318 and the crimping ring 320 are identical or substantially similar to the respective anchor member 4, spacer 10, pressure washer 11, sleeve 12, bumper 18 and crimping ring 20 of the assembly 1 and therefore shall not be discussed in great detail herein. The sleeve 312 has a curved inner surface 354 substantially similar to the curved inner surface 54 previously described herein with respect to the sleeve 12. The sleeve 316 has a curved inner surface 355 that is also substantially similar to the curved inner surface 54 previously described herein with respect to the sleeve 12. In substantially all other aspects of form and function, the sleeve 316 is substantially similar to the sleeve 16 previously described herein with respect to the assembly 1. The sleeve 312 includes a pair of opposed end plates 358 and 360 and the sleeve 316 includes a pair of opposed end plates 362 and 363. The illustrated plates 358, 360, 362 and 363 have outer cylindrical surfaces 364, 366, 368 and 369, respectively, that are substantially smaller in diameter than an outer diameter of the spacer 314 and the washers 313 and 315, allowing gaps for greater relative tilting or articulation of the sleeves 312 and 316 with respective adjacent washers 313 and 315, as will be described in greater detail below.

Thus, the assembly 301 primarily differs from the assembly 1 in the geometry of the washers 313 and 315 and the spacer 314. The elastic spacer 314 is substantially similar to the spacer 14 in form, function and materials with the exception that rather than having opposed planar side surfaces 90 and 91, the spacer 314 has opposed side surfaces 390 and 391 that are curved and concave. In particular, the illustrated surfaces 390 and 391 are cupped shaped, sized and shaped to closely slidingly mate with the dome shaped washers 313 and 315, as will be described in greater detail below, allowing for articulating movement between the spacer 314 and the washers 313 and 315, in addition to compression of the spacer 314.

The pressure washers 313 and 315 are identical to one another and also are substantially similar to the pressure washer 11 previously described above with the exception that the washers 313 and 315 have opposed, curved, convex side surfaces sized and shaped for cooperation with a substantially concave surface of a cooperating sleeve 312 or the concave surfaces 390 or 391 of the spacer 314. The illustrated washer 313 has opposed curved surfaces 402 and 404 and the washer 315 has opposed curved surfaces 402' and 404'.

The assembly 301 is assembled in a manner substantially similar to the manner of assembly previously described herein with respect to the assembly 1. Also, similar to what has been described previously with respect to the assembly 1, the core 306 may initially be of a longer length measured along the axis AAA than is shown in the drawing figures, allowing for a manipulation tool to grasp the core 306 near an end thereof that extends through the crimping ring bore. The spacers 310 and 314 and the bumper 318 are compressed, followed by deformation of the crimping ring 320 against the core 306. Then, the coverings 322 and 323 are fabricated on the assembly 301 at the locations shown in the figures and as described above. The assembly 301 is now in dynamic relationship with the spacers 310 and 314, washers 311, 313 and 315, sleeves 312 and 316 and bumper 318 being slidable with respect to the core 306, both sleeves 312 and 316 being more readily movable in a direction toward the bumper 318 due to the greater elasticity of the bumper 318 as compared to the spacers 310 and 314.

The assembly 301 may then be implanted, cooperating with three bone screws 25 as previously illustrated with respect to the assembly 1. Like the assembly 1, the assembly 301 provides for a dynamic and flexible connection between three bone anchors. Furthermore, the double domed articulating wear washers 313 and 315 cooperating with the cupped spacer 314 allow for increased flexion and extension over the assembly 1 having the spacer 14 with planar surfaces. While the assembly 1 spacer 14, for example, elastically compresses when the assembly bends during spinal flexion or extension, the pressure washers 313 and 315 may slidingly articulate along the surfaces 390 and 391 of the spacer 314 during spinal flexion or extension. If compression accompanies the bending movement, the spacer 314 may also compress slightly in response to the spinal movement. As illustrated in FIG. 47, the end plates 358 and 360 of the sleeve 312 and the end plates 362 and 363 of the sleeve 316 are sized and shaped to have a smaller outer diameter than the pressure washers and spacers of the assembly 301 as well as provide a gap between such plates and adjacent components of the assembly 301, providing clearance for articulated movement between the components.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having first and second bone attachment structures cooperating with a longitudinal connecting member, the improvement wherein the longitudinal connecting member comprises:
   a) an anchor member portion passing through and secured directly to the first bone attachment structure, the anchor member portion having a first width and having an integral core extension of reduced second width, the core extension extending from the anchor member portion along a substantially central axis of the longitudinal connecting member, the first and second widths being measured perpendicular to the central axis;

b) a first elastic outer spacer, the core extension being received in the spacer, the spacer being positioned between the two bone attachment structures;

c) a second elastic outer spacer, the core extension being received in the second spacer, the second spacer being more compressible than the first spacer, both the first and second spacers being pre-compressed prior to attachment of the assembly to the bone attachment structures; the second elastic outer spacer being located relative to the core extension so as to not be between the first and second bone attachment structures; and d) a substantially inelastic sleeve, the core extension being received through the sleeve and in slidable relationship therewith, the sleeve passing through and secured in the second bone attachment structure, the sleeve being disposed between the first and second pre-compressed spacers, the pre-compressed spacers exerting axial forces on the sleeve.

2. The improvement of claim 1 wherein the second spacer is disposed near an end of the assembly.

3. The improvement of claim 2 further comprising a fixing structure engaged with the core extension at an end thereof opposite the anchor member portion and adjacent the second spacer.

4. The improvement of claim 3 wherein the fixing structure is a crimping ring fixed to the core extension.

5. The improvement of claim 1 wherein the core extension has a substantially circular cross-section measured perpendicular to the axis.

6. The improvement of claim 1 wherein the core extension has a non-circular cross-section measured perpendicular to the axis.

7. The improvement of claim 1 wherein the anchor member portion has a substantially circular cross-section measured perpendicular to the axis.

8. The improvement of claim 1 wherein the first spacer has opposed parallel load-bearing end surfaces disposed substantially perpendicular to the axis.

9. The improvement of claim 1 wherein the first spacer has opposed non-parallel load-bearing end surfaces.

10. The improvement of claim 9 wherein the first spacer has a curved load bearing surface.

11. The improvement of claim 9 wherein the first spacer has a planar load bearing end surface disposed substantially perpendicular to the central axis and a curved opposed load bearing end surface.

12. The improvement of claim 1 wherein the core extension is substantially linear.

13. The improvement of claim 1 wherein the core extension is integral to the anchor member portion.

14. The improvement of claim 1 further comprising at least one pressure washer located adjacent the sleeve, the pressure washer having a substantially convex surface sized and shaped to slidingly engage a substantially concave surface of the sleeve.

15. The improvement of claim 14 wherein the convex surface is at least partially spherical.

16. The improvement of claim 15 wherein the concave surface is at least partially spherical.

17. The improvement of claim 14 wherein the at least one pressure washer is a first pressure washer and further comprising a second pressure washer, the first pressure washer located adjacent one end of the sleeve and the second pressure washer located adjacent an opposite end of the sleeve.

18. The improvement of claim 1 wherein the first spacer is made from a material having a higher durometer than a material of the second spacer.

19. The improvement of claim 18 wherein the first spacer has at least one groove.

20. The improvement of claim 1 wherein the first spacer has a different geometry than the second spacer.

21. The improvement of claim 1 further comprising at least a third elastic and pre-compressed spacer.

22. The improvement of claim 1 wherein the at least one sleeve has an inner surface defining a through bore, the core extension being received in the through bore and in sliding relation with the sleeve inner surface, the sleeve inner surface being substantially cylindrical.

23. The improvement of claim 1 wherein the at least one sleeve has an inner surface defining a through bore, the core extension being received in the through bore and in sliding relation with the sleeve inner surface, the sleeve inner surface being non-linear in cross-section taken along the central axis, the surface flaring radially outwardly towards at least one of the first and second spacers.

24. The improvement of claim 23 wherein the sleeve inner surface is hyperboloid.

25. The improvement of claim 1 further comprising an elastic over-mold covering at least a portion of the at least one sleeve and adjacent first compressible outer spacer.

26. The improvement of claim 1 further comprising an elastic over-mold substantially covering at least one of the first and second spacers.

27. The improvement of claim 1 wherein the second spacer has non-overlapping engagement with the sleeve.

28. The improvement of claim 1 wherein the first spacer has a central compression member flanked by a pair of washers.

29. The improvement of claim 28 wherein the relative stiffness and displacements of the central compression member and washers is variable so as to be adjustable for specific pertinent requirements.

30. The improvement according to claim 1, wherein the sleeve includes a cup shaped end surface.

31. In a medical implant assembly having first and second bone anchors cooperating with a longitudinal connecting member, the improvement wherein the longitudinal connecting member comprises:

a) an anchor member portion having a first width and also having an integral inner core extension having a second width that is smaller than the first width and extending from the anchor member portion along a central axis thereof; the anchor member portion passing through and being secured to the first bone anchor; the extension slidably passing through the second bone anchor;

b) an elastic and pre-compressed outer spacer, the longitudinal connecting member being slidingly received through the spacer along the axis, the spacer being positioned between the bone anchors, the spacer having at least a first curved end surface;

c) at least one inelastic sleeve, the core extension being slidingly received within the sleeve along the axis, the sleeve being in engagement with the second bone anchor, the sleeve having at least a second curved end surface; and d) at least one elastic and pre-compressed bumper disposed near an end of the core extension and not between the first and second bone anchors, the elastic bumper being more elastic than the spacer, allowing for the sleeve to move back and forth along the core a greater distance toward the bumper than toward the spacer.

32. The improvement of claim 31 further comprising at least one pressure washer having at least a third curved end surface sized and shaped to closely slidingly cooperate with one of the first curved end surface and the second curved end surface.

33. The improvement of claim 32 wherein the third curved end surface is substantially convex and the first and second curved end surfaces are substantially concave.

34. The improvement of claim 32 wherein the first, second and third curved surfaces are all at least partially spherical.

35. The improvement of claim 31 wherein the at least one outer spacer is a plurality of spacers of differing degrees of elasticity.

36. The improvement of claim 35 wherein the differing degrees of elasticity are due to differences in durometer between the spacers.

37. The improvement of claim 35 wherein the differing degrees of elasticity are due to difference in geometry between the spacers.

38. The connecting member according to claim 31, wherein the sleeve curved end surface is cup shaped.

39. In a medical implant assembly having first and second bone anchors cooperating with a longitudinal connecting member, the improvement wherein the longitudinal connecting member comprises:
   a) an anchor member portion having a first width, the anchor member having a core extension of a second smaller width extending therefrom along a central axis thereof, the first and second widths measured in a direction perpendicular to the axis; the anchor member portion passing through and being secured to the first bone anchor; the core extension slidably passing through the second bone anchor in use;
   b) an elastic outer spacer, the core extension being slidingly received through the spacer along the axis, the spacer being positioned between the at least two bone anchors; and
   c) an inelastic sleeve, the core extension being slidingly received within the sleeve along the axis, the sleeve being secured to the second bone anchor, the sleeve having an inner surface defining a through bore for receiving the core extension.

40. The improvement of claim 39 wherein the sleeve inner surface flares radially outwardly in a direction toward the at least one compressible outer spacer.

41. The improvement of claim 39 wherein the sleeve inner surface is hyperboloid in shape.

42. The improvement of claim 39 further comprising at least one inelastic pressure washer having a convex surface sized and shaped to closely slidingly cooperate with at least a portion of the sleeve inner surface.

43. The improvement of claim 42 further comprising an elastic over-mold covering at least a portion of the pressure washer and at least a portion of the sleeve.

44. The improvement of claim 39 wherein at least a portion of the sleeve inner surface is non-linear in cross-section taken along the axis.

45. The connecting member according to claim 39, wherein the sleeve includes a cup shaped end surface.

46. A medical implant comprising:
   a) first and second bone anchors;
   b) a longitudinal connecting member having a first non-sliding anchor portion of a first width that passes through and is secured to the first bone anchor;
   c) the connecting member has a second integral extension portion that extends axially from the first anchor portion; the extension portion having a second width that is less than the first width,
   d) a sleeve slidably receiving the extension portion that is mounted in the second bone anchor such that the extension portion passes through and is slidably received in the second bone anchor;
   e) an end blocker secured to the connecting member; and
   f) a bumper located between the blocker and the second bone anchor; the sleeve and the bumper being pre-compressed.

47. The connecting member according to claim 46, wherein the sleeve includes a cup shaped end surface.

48. In a medical implant assembly having first and second bone attachment structures cooperating with a longitudinal connecting member, the improvement wherein the longitudinal connecting member comprises:
   a) an anchor member portion passing through and secured directly to the first bone attachment structure, the anchor member portion having a first width and having a core extension of reduced second width, the core extension extending from the anchor member portion along a substantially central axis of the longitudinal connecting member, the first and second widths being measured perpendicular to the central axis;
   b) a first elastic outer spacer, the core extension being received in the spacer, the spacer being positioned between the two bone attachment structures;
   c) a second elastic outer spacer, the core extension being received in the second spacer, the second spacer being more compressible than the first spacer, both the first and second spacers being pre-compressed in a resting assembly state when connected to the bone attachment structures; the second elastic outer spacer being located relative to the core extension so as to not be between the first and second bone attachment structures; and
   d) a substantially inelastic sleeve, the core extension being received through the sleeve and in slidable relationship therewith, the sleeve passing through and secured in the second bone attachment structure, the sleeve being disposed between the first and second pre-compressed spacers, the pre-compressed spacers exerting axial forces on the sleeve.

49. The improvement according to claim 48, wherein the sleeve includes a cup shaped end surface.

* * * * *